US008049071B2

(12) United States Patent
Gao et al.

(10) Patent No.: US 8,049,071 B2
(45) Date of Patent: Nov. 1, 2011

(54) SOYBEAN PLANT AND SEED CORRESPONDING TO TRANSGENIC EVENT MON87701 AND METHODS FOR DETECTION THEREOF

(75) Inventors: Ai-Guo Gao, Chesterfield, MO (US); Kathryn H. Kolacz, Manchester, MO (US); Ted C. MacRae, Wildwood, MO (US); John A. Miklos, Des Peres, MO (US); Mark S. Paradise, St. Louis, MO (US); Frederick J. Perlak, Kapolei, HI (US); Andrea S. Toedebusch, Labadie, MO (US); Leslie A. Harrison, Wildwood, MO (US)

(73) Assignee: Monsanto Technology LLC, St. Louis, MO (US)

( * ) Notice: Subject to any disclaimer, the term of this patent is extended or adjusted under 35 U.S.C. 154(b) by 78 days.

(21) Appl. No.: 12/265,860

(22) Filed: Nov. 6, 2008

(65) Prior Publication Data

US 2009/0130071 A1 May 21, 2009

Related U.S. Application Data

(60) Provisional application No. 60/988,349, filed on Nov. 15, 2007.

(51) Int. Cl.
*A01H 5/00* (2006.01)
*A01H 5/10* (2006.01)
*A01H 1/00* (2006.01)
*C12N 15/82* (2006.01)

(52) U.S. Cl. ............... 800/312; 536/23.71; 800/267; 800/260; 426/615

(58) Field of Classification Search ............... None
See application file for complete search history.

(56) References Cited

U.S. PATENT DOCUMENTS

| | | | |
|---|---|---|---|
| 6,063,756 | A | 5/2000 | Donovan et al. |
| 6,893,826 | B1 | 5/2005 | Hillyard et al. |
| 7,332,594 | B2 | 2/2008 | Baum et al. |
| 2007/0061919 | A1 | 3/2007 | Baum et al. |

FOREIGN PATENT DOCUMENTS

| | | |
|---|---|---|
| AR | 010897 B1 | 2/2009 |
| CN | 1950509 A | 4/2007 |
| EP | 0 385 962 A1 | 9/1990 |
| WO | WO 02/40677 A2 | 5/2002 |
| WO | WO 02/100163 A2 | 12/2002 |
| WO | WO 2005/061720 A2 | 7/2005 |
| WO | WO 2006/130436 A2 | 12/2006 |

OTHER PUBLICATIONS

Muzny et al (2002, GenBank Accession No. AC120328).*
Stewart et al (1996, Plant Physiol. 112:121-129).*
John Miklos et al., "Characterization of Soybean Exhibiting High Expression of a Synthetic *Bacillus thuringiensis* cry1A Transgene that Confers a High Degree of Resistance to Lepidopteran Pests," Crop Sci., 47:148-157 (2007).
Ted Macrae et al., "Laboratory and Field Evaluations of Transgenic Soybean Exhibiting High-Dose Expression of a Synthetic *Bacillus thuringiensis* cry1A Gene for Control of Lepidoptera," J. Econ. Entomol, 98(2):577-587 (2005).
Litao Yang et al., "Qualitative and quantitative PCR methods for event-specific detection of genetically modified cotton Mon1445 and Mon531," Transgenic Research 14:817-831 (2005).
Litao Yang et al., "Event-Specific Quantitative Detection of Nine Genetically Modified Maizes Using One Novel Standard Reference Molecule," J. Agric. Food Chem., 55:15-24 (2007).
Litao Yang et al., "Event Specific Qualitative and Quantitative Polymerase Chain Reaction Detection of Genetically Modified MON863 Maize Based on the 5'-Transgene Integration Sequence," J. Agric. Food Chem., 53:9312-9318 (2005).
Askild Hoick, "5'-Nuclease PCR for quantitative event-specific detection of the genetically modified Mon810 MaisGard maize," Eur Food Res Technol, 214:449-453 (2002).
Aihu Pan et al., "Event-specific qualitative and quantitative PCR detection of MON863 maize based upon the 3'-transgene integration sequence," Journal of CerealI Science, 43:250-257 (2006).
English specification of Argentina Patent Application No. P980100818 filed Feb. 24, 1998.
Final Office Action regarding U.S. Appl. No. 11/801,114, dated Aug. 26, 2009.
New England BioLabs Inc., 1998/99 Catalog, Nucleic Acids, Linkers and Primers, pp. 121 and 284.

* cited by examiner

*Primary Examiner* — Anne Kubelik
(74) *Attorney, Agent, or Firm* — Timothy K. Ball, Esq.; SNR Denton US LLP

(57) ABSTRACT

The present invention provides a transgenic soybean event MON87701, and cells, seeds, and plants comprising DNA diagnostic for the soybean event. The invention also provides compositions comprising nucleotide sequences that are diagnostic for said soybean event in a biological sample, probes and primers for use in detecting nucleotide sequences that are diagnostic for the presence of said soybean event in a biological sample, and methods for detecting the presence of said soybean event nucleotide sequences in a biological sample. The invention further provides methods of growing the seeds of such soybean event into soybean plants, and methods of breeding to produce soybean plants comprising DNA diagnostic for the soybean event.

24 Claims, 2 Drawing Sheets

SEQUENCE LISTING

```
<160> NUMBER OF SEQ ID NOS: 16

<210> SEQ ID NO 1
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: 5' Junction Sequence

<400> SEQUENCE: 1
```

```
ttagtgtgtg tgtcaaacac                                              20

<210> SEQ ID NO 2
<211> LENGTH: 20
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(20)
<223> OTHER INFORMATION: 3' Junction sequence

<400> SEQUENCE: 2
atgaagccat caaaaagtag                                              20

<210> SEQ ID NO 3
<211> LENGTH: 6285
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(6285)
<223> OTHER INFORMATION: 5' Flanking Sequence Plus Junction

<400> SEQUENCE: 3
gggaaaatcc ctcttccata ttaagaacat aaaaatcaac aggaaaaata agttcaccaa    60
cccgaaccag cacatcctct atgaaacctg cggggtaagc agcacttcta ttttccaaat   120
gaatcaccac atctgtagat tgcaaaggtc caagagataa agaattgaaa atggacagag   180
gggtgacact aactgatgct cctagatcta gcattgtatt atcaaattta ctgttcccaa   240
taatgcaagg tatacagaaa gtacctgggt ccttacattt ctcaggaatg taaggaacaa   300
atttacctat caatgctgac acatttctgc ccatgctaat cctttcattg cctttgagct   360
tccttttgtg ggtgcacaac tcctttagaa acttgacaca tcttggaatc tgcttgatgg   420
catctagcag aggtatgttc acctctactt tcctgaaggt ctccaagatc tccttttctg   480
cttcttccat tttttttgtt tggaattgct caaggttgga atggaagagg ataagaggc    540 tgcggtaagt cagaattact agaagaaggt ccacctgcat gaaaattttt gttaggaagc   600
tttctctttt gtgcaactat ctcatcctct ttttcaggtg tagaatgaag cttgacaggt   660
tcaggtgcgg gtgctgctac tggtggaggt acttgaattt ggttgtcaga cctcaaggtg   720
atgcactcca cattttcgg attttgcaca gtttgtgaag gcaatttgtc agaatttgg    780 gaatgagctt ggttcaactg agtagccatc cgccccatct gatttgtcag actctgaatg   840
aaggctcttg tctcttgctg aaattgcata ttctggatgg tcatttgcct cactaactct   900
tctaaggaag gttaaggagg agtctcagtt gcttgttgtc tttgttgtga ctgttgttgt   960
tgttgctgct gtattggagg aggaacatat ggtttgcttg gaccagcaac attctggaaa  1020
ggagggacag actgttgttg ttgtgaagga cttgcccatc tcatatttgg atgatttctc  1080
caacctggat tgtatctgtt gcttggaaga tcataattat tttgctattg ttggtttgc   1140 tgttgagggg gtctattata aatgtttgca gcataagctt caggttgttc attgactcca  1200
gattactgca aagaaggaca agatctgta tggtgatctg cagaagaaca tataccacag   1260
actcttgtaa caggtgcaaa tttctgattc atggcaagct gagttactag gttgaccaag  1320
gcatcaagtt tccctcaag cttttttattt tcagtagata aagatgaatc tgtggccacc  1380
tcatcgactc ctctaaggac aatagcatca tttcttgcac tgaattgttg ggagttggaa  1440
```

```
gccttcttct caatcaaatt cctagcctca gcagggtca tatcacgaag agctccacca    1500
ctggcagcat caatcatact cctctccatg ttgctaagtc cctcatagaa atattgaaga    1560
aggagttgct cagaaatctg gtggtgagga cagcttgcac acaatttctt gaatcttttct  1620 cagtactcat acaagctctc tccactaagt tgcctgatgc ctgaaatttc ttttctgatg    1680
gcagtggtcc tagatgcagg gaagaatttc tccaagaaca ccctcttaag gtcatcccag    1740
ctgaaaatgg acctgggagc aaggtagtag agccaatctt ttgtcactac ctccagagaa    1800
tgaggaaaag cctttagaaa gatatgatct tcttggacat caggggggctt catggtggaa   1860 caaacaatat ggaactcctt aagatgctta tgaggatctt cacctagaag accatgaaac    1920
ttgggtagca aatgtattag tccagtcttg agaacatatg gaacaccctc atcaggatat    1980
tgaatgcaca gttttcata agtgaaatca ggtgcagcca tctccctaag agtcctctca    2040
cgaggtggag gtttagccat gttctcagta tgaaaattag tagttgaatg ctcaaaatca    2100
gaatattcag aatcaccaga aacaaaatac tcagaatgct caaatgctc aaaatgcaca     2160 taatgattag gatgcacact atgcctaact aatctatgaa aggttctatc tatttcagga    2220
tcgaagggtt ataaatcacc tagattgccc ctagtcatgc actatatgta gcaaataatg    2280
tgttctcaaa caagcaccaa gggagggtta aaactacaac tatagtcaaa tgatatccaa    2340
atgagttgaa attttgtgag cagcacccta aaatcatgaa aagatagcac aaaaaatttc    2400
aaacgaaaat tcaaagtcta actatgaaaa ctacttaaga aagtttaga aaaataggac     2460 aataatactt gaaaataaaa aaaaaacata gtaaacagct gattttcga gtttgggaga    2520 ctccaaccgg ctaaaacggg ttgccacaat atgagaaatt ttttctacc ccaaatgcca     2580 caatatgaga aagttttgct aaaatcagt tcccaaaatt tttgtctctc tcaaattcaa     2640
ccacaccaag tgctcctagt attttcaca caaaaaatca gccaaaaata caactctaa     2700 ctatcaaaac aaaaacagct aattaaattg caaaatcagt cgctaattcc tagtcactaa    2760
tcactgttca cagcaaaaca ccaactgaat cagtcgctaa acagtcgcta aacaggagac    2820
gcaactgaaa tgcaaaacag aatgctacac aaaacaaaac aactaaacac tattatgaac    2880
ctttggccca ctgctccccg acaacggcgc caaatttgat cgaggtcgta cccgaatcaa    2940
ataaacatta aaaatgcagt atctaggaag tgatcctagg tcatctccca acgagcaatg    3000
gtcaaccaat gttcataata gatagtgata aaacaataac gaattggggg gggggggtat    3060 ttgttttgt aatttaaaca acaagcaaat tttaattaga aaataacaga attaaaacat     3120
gttatttccc cttgattcat aagcaagtct cttatcctag gttaggagga tttatcccta    3180
accagttcaa ccacttaatc caaccctaaa ttaaattact aagcgaaaat taacataagg    3240
ttgtctttat atgattaagc aacacataca ccaattaatc atgaacaaaa tcgatcatta    3300
agcatcaaca taaattaagc gcaaagataa ttaatcaagc actaagcatg catggattag    3360
tagcaacaaa tacagagtaa ttggtggaga tgaaaaactg atcaatattc aatagtaata    3420
acaaaacctc aaagagagtt gtgcttgatt ctcaagagaa acaacgctg gagacttagc     3480 cttccattaa tcagtagaaa acgaaattgt agaaaacgaa ttttattcta tgtgaacaat    3540
gtgcatgaac agtaataaaa actggaattg caaaacccta aaattattct tctctccaaa    3600
aaaactccct aaactaaaac cctggtgcta ttatataggt cctcagcccc aaagcttaca    3660
aatctatttt cagtccaaac ccataaacga aataaaataa aatctggaca agataagata    3720
agattggatg aaataaaatc tggacgaaat aaaatctgga taagataaga tttgataaaa    3780
taaaattgtc tgctcttttc aagtccaagc ccaattccgg attcaagccc aattttttat    3840
```

```
aattcttctg aaattaaatt aaaaatacga aattagtcaa gtaggcccaa atgataaaac    3900
tgcataatta atttgacaat taaggctaat cagtaattaa aatagtgaca aaaagggtta    3960
agaaatagga gaataatgac acatcaccca tatggggagc aattctaaaa tgcatttgag    4020
ttctttaacc tgagacacag tgcagtagag tctccaagga ttcattgtgc cttttatttt    4080
atatgatggg gtcactacat tggccttgtc aaagaaactg aatttggggg attaaagaaa    4140
cacaaaataa aaacaaatga aactagttaa tagaaatgtt gcctattgct tcttggaaaa    4200
agtccaacca tttgtgattt ggataaaatt catattaccc acttgtagct tgttcaatca    4260
aacactagat ttggataaaa tctcactcct agatatacct caagggataa tatgaccaac    4320
attagtcatt tttagaaagt aaagtggaca aatttgagat ttcattcctt aatgacatta    4380
taaacatgta ttttttccat gaccctttt caatgtaagt acaatttatc ccttagttta    4440
gatactctat atatgcatgt tacgtagttg atgaaaacat acctaagttg ttgtgtatgg    4500
ttaagtttgc gactacctct gatatcaaac tcctcatctc caatctcata caaaagatac    4560
ttgtcacttg gtacctgaac cttgtcagtt tgcagttgtg agtttcttct gaagccacac    4620
gcttgtatag taaccagaag ccaggaggga gtcctctaag gctctaactc gtattttccg    4680
tggaagtaca ttttttttct taaagaaaac agagatagtt taccaatgat aatatttctt    4740
tagccaaata ggaccatcat agaaaacaaa actcttcttc taagtattta atgcaactac    4800
atatttaggg tgcgtttgat tcgctaaaaa ataagggtct agacaacaca aaaatatttt    4860
tccaacgttt gattttaaaa atggctgaga gacaatacaa aataaagaat gatgaactgg    4920
acaaaaacct aaaaacttgt aactcactga atctcataca actttttgtt cagtgtctaa    4980
aaaaagtaaa aatacaatat tattcctatt ttttactttg attatctcac accttctttc    5040
tactcatttg tttcacttca cctctccagt gggcaccttg gtttgtcggc gagagtcgta    5100
tggacttttg ttgttccctt tttgctcatt atttctttct tttcattgtt aatttattca    5160
aatgttccca tcatcatctt actccttctt gttatgtttt ttttctttgg ccaactccaa    5220
cgaggccgtg ccgcgaccac catcatcacg accttatggc ggcctcacgc cgcaaggccc    5280
tgcacccagt ggcatcaggg gtcatgcctc cttcttaaag gtgtctctct tttgttatgt    5340
cgtcaaagtg ttgctaattc acctagaatt tttcaatgaa tcccttact tgtgggttag    5400 tctaggtcgc tctgcccggt tccaacccta gcccaaaaaa aaatgaaatg ggtaggaaag    5460
gcgggcctag tttgaattaa aataaatcat gctaagatat tgataactgc tatgtatagg    5520
tatattttgg gattaaatta tataggaatt agtaattttt ctctcttatt tcttcctttt    5580
tgttcaaata attggaattc taacatcatt taagttttta tgtagaaaat attaaaagtt    5640
gatgaattta tgatacttag tgaataatta gagtagaaaa ataagtaaa gcccaaaaaa    5700 gaaaattggt gatatgaaga tacatgctta gcatgcccca ggcacgctta gtgtgtgtgt    5760
caaacactga tagtttaaac tgaaggcggg aaacgacaat ctgatcccca tcaagcttga    5820
tatcgaattc ctgcagcccg ggggatccac tagttctaga gcggccgcgt taactgcagg    5880
tcgacggatc cccgggtacc gagctcgaat tcaaatttat tatgtgtttt ttttccgtgg    5940
tcgagattgt gtattattct ttagttatta caagactttt agctaaaatt tgaaagaatt    6000
tactttaaga aaatcttaac atctgagata atttcagcaa tagattatat ttttcattac    6060
tctagcagta ttttttgcaga tcaatcgcaa catatatggt tgttagaaaa aatgcactat    6120
atatatatat attatttttt caattaaaag tgcatgatat ataatatata tatatatata    6180
tatgtgtgtg tgtatatggt caaagaaatt cttatacaaa tatacacgaa cacatatatt    6240
```

-continued

| tgacaaaatc aaagtattac actaaacaat gagttggtgc atggc | 6285 |

<210> SEQ ID NO 4
<211> LENGTH: 2611
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(2611)
<223> OTHER INFORMATION: 3' Flanking Sequence Plus Junction

<400> SEQUENCE: 4

| gactgacaag atcgatctga agtctaaaca attctaagag gtatcatgta gcaatgtcct | 60 |
| gccacaatat tgaattgacc tgcagcccgg gcggccgcat cgatcgtgaa gtttctcatc | 120 |
| taagccccca tttggacgtg aatgtagaca cgtcgaaata aagatttccg aattagaata | 180 |
| atttgtttat tgctttcgcc tataaatacg acggatcgta atttgtcgtt ttatcaaaat | 240 |
| gtactttcat tttataataa cgctgcggac atctacattt ttgaattgaa aaaaaattgg | 300 |
| taattactct ttcttttcct ccatattgac catcatactc attgctgatc catgtagatt | 360 |
| tcccggacat gaagccatca aaagtaggac taatttagg aaagcaagct aattcaagaa | 420 |
| agtgaaggca cgcttagtgt gagacacgtg ttgagcgcga ttactgccac tcactaacca | 480 |
| cacaagtgca ctcagtgcga aggttgctta aaaattaagt tgattcgcac ttataaaga | 540 |
| aggatagaga tgaaggaaaa aacacagaaa atacaattcc ttatagaaga caaaggctag | 600 |
| aagaagcaaa cgcaaacatt agaagtcatt ccttccctca attccttttt tcaatttccc | 660 |
| cttttactaa atattctcct cttgcaatta taaagcctcc tatgacaatg acaagctaaa | 720 |
| ctctcctttg ttgggaactt atcagtcaac tgctcttaat ataatttctc ttcctatcta | 780 |
| ttatgaatat tcactacaag aaatatgccc atttgccagg gattttgac agggacatta | 840 |
| acccctggca aatttcccag ggactaagcc aaggaaaccc ctggcaaaat gacatttgag | 900 |
| aaggctggga ccacttacat ttacacaggg gtttgtccct cgcaaaaata caaaagcctt | 960 |
| ggcaaaaaaa agagcgggaa atgaatttta aaacagcatg ttgttttcac acagccaaac | 1020 |
| acacgggtat gccctcgttt tctgtaaagc tgacggaatc ttcccataag tcaacacgac | 1080 |
| atgaccatgc actgcaaaaa gctgtgcggc ccagacgtga caggggtgtt accctcgga | 1140 |
| aatggcttgc agcccctggc aaaaaggaat ccctgctttc ctagctacac cgttctgctc | 1200 |
| atatagctga agctaggagg ttagcctttg actctgttgt tttgcgaggg gcattccgtg | 1260 |
| agttattccc tgggtttttt tacactatat agccaaaccg cgtgtttatc ctcatgctca | 1320 |
| gtgttgtgtt tttgaaactt agaaaaattt tcggtttcca tttccatcct caccagttca | 1380 |
| ttttcagtcc attatcattc agttcataca cttgttctat aatttggtaa cactctttc | 1440 |
| acttattata ttttctgtt tttatttgtt actacttatt aacataaata ttttttattg | 1500 |
| tatcagtgtc caaatttgcc tcctcctgct gctccttgct ctctgaattt gttctcttaa | 1560 |
| gcttcaacaa gttagtaatt tttctactta aattttaga tatatgatgt ttatatatat | 1620 |
| gatgttataa ttttgcatga tctgtcaaag aaaatatgat gtttctactt gcatgatgtg | 1680 |
| ttataatata tgatgtttat atatatttcg aattttgttg ttaataaaac tgtttaatta | 1740 |
| gaaactgtat aatttttttg tttaataaaa ctgtttaatt ttgcatgatc tgtttaataa | 1800 |
| aactgtttat ataaactgt ttatatataa tatgatgt taacatttt aaaactgttt | 1860 |
| ataaaacagt ttagttagaa aaaatgttaa aactagagaa aaaaatgtat aataaaactg | 1920 |

| | |
|---|---|
| tgtcagtaca gcagcgcgtc agaaaagtgt gcagatgcgt cagtgagaag acaggggcta | 1980 |
| agacagggat tttgacaggg aattttgcca gggattttgc cagggtcagc ccctcgtttt | 2040 |
| tttgccaggg gtgaaatccc tggcaaactg atttgcgatg ggcgttttc ccagggattc | 2100 |
| agccctggc aaaatccctg gcaaacgtcc atttcccagg gcttttgtt cttttcccag | 2160 |
| ggaatccgcc cctggcaaac gagcttgttt cttgtagtga ttacttttgc attagttttt | 2220 |
| cctgtattta attttattgt ttatggcttg attacccatt tgcattataa gttttagggg | 2280 |
| tagcgttgaa aagtgttatt ctctaataga actggaaaag agtatttaaa taacttcatc | 2340 |
| actagggata cattgatttt atttagctta ttatatatct ctattattaa tgtaatttaa | 2400 |
| ctattttatc tctgcaaagt gatttgggag agaagataga taagttagac tctttcactc | 2460 |
| gaggctgagt acaaccttga gagagcccag aaggctgtga acgccctctt tacctccacc | 2520 |
| aatcagcttg gcttgaaaac taacgttact gactatcaca ttgaccaagt gtccaacttg | 2580 |
| gtcacctacc ttagcgatga gttctgaagg g | 2611 |

<210> SEQ ID NO 5
<211> LENGTH: 6426
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(6426)
<223> OTHER INFORMATION: Inserted DNA Sequence

<400> SEQUENCE: 5

| | |
|---|---|
| tgtcaaacac tgatagttta aactgaaggc gggaaacgac aatctgatcc ccatcaagct | 60 |
| tgatatcgaa ttcctgcagc ccgggggatc cactagttct agagcggccg cgttaactgc | 120 |
| aggtcgacgg atccccgggt accgagctcg aattcaaatt tattatgtgt ttttttttccg | 180 |
| tggtcgagat tgtgtattat tctttagtta ttacaagact tttagctaaa atttgaagaa | 240 |
| atttacttta agaaaatctt aacatctgag ataatttcag caatagatta tattttttcat | 300 |
| tactctagca gtattttttgc agatcaatcg caacatatat ggttgttaga aaaaatgcac | 360 |
| tatatatata tatattattt tttcaattaa aagtgcatga tatataatat atatatatat | 420 |
| atatatgtgt gtgtgtatat ggtcaaagaa attcttatac aaatatacac gaacacatat | 480 |
| atttgacaaa atcaaagtat tacactaaac aatgagttgg tgcatggcca aaacaaatat | 540 |
| gtagattaaa aattccagcc tccaaaaaaa aatccaagtg ttgtaaagca ttatatatat | 600 |
| atagtagatc ccaaattttt gtacaattcc acactgatcg aattttttaaa gttgaatatc | 660 |
| tgacgtagga tttttttaat gtcttacctg accatttact aataacattc atacgttttc | 720 |
| atttgaaata tcctctataa ttatattgaa tttggcacat aataagaaac ctaattggtg | 780 |
| atttatttta ctagtaaatt tctggtgatg ggctttctac tagaaagctc tcggaaaatc | 840 |
| ttggaccaaa tccatattcc atgacttcga ttgttaaccc tattagtttt cacaaacata | 900 |
| ctatcaatat cattgcaacg gaaaaggtac aagtaaaaca ttcaatccga tagggaagtg | 960 |
| atgtaggagg ttgggaagac aggcccagaa agagatttat ctgacttgtt ttgtgtatag | 1020 |
| tttttcaatgt tcataaagga agatgggagac ttgagaagtt ttttttggac tttgtttagc | 1080 |
| tttgttgggc gttttttttt ttgatcaata actttgttgg gcttatgatt tgtaatatt | 1140 |
| tcgtggactc tttagtttat ttagacgtgc taacttgtt gggcttatga cttgttgtaa | 1200 |
| catattgtaa cagatgactt gatgtgcgac taatctttac acattaaaca tagttctgtt | 1260 |

```
ttttgaaagt tcttattttc attttttattt gaatgttata tattttttcta tatttataat    1320 tctagtaaaa ggcaaatttt gcttttaaat gaaaaaaata tatattccac agtttcacct    1380
aatcttatgc atttagcagt acaaattcaa aaatttccca tttttattca tgaatcatac    1440
cattatatat taactaaatc caaggtaaaa aaaaggtatg aaagctctat agtaagtaaa    1500
atataaattc cccataagga aagggccaag tccaccaggc aagtaaaatg agcaagcacc    1560
actccaccat cacacaattt cactcataga taacgataag attcatggaa ttatcttcca    1620
cgtggcatta ttccagcggt tcaagccgat aagggtctca acacctctcc ttaggccttt    1680
gtggccgtta ccaagtaaaa ttaacctcac acatatccac actcaaaatc caacggtgta    1740
gatcctagtc cacttgaatc tcatgtatcc tagaccctcc gatcactcca aagcttgttc    1800
tcattgttgt tatcattata tatagatgac caaagcacta gaccaaacct cagtcacaca    1860
aagagtaaag aagaacaatg gcttcctcta tgctctcttc cgctactatg gttgcctctc    1920
cggctcaggc cactatggtc gctccttttca acggacttaa gtcctccgct gccttcccag    1980
ccacccgcaa ggctaacaac gacattactt ccatcacaag caacggcgga agagttaact    2040
gcatgcaggt gtggcctccg attggaaaga agaagtttga gactctctct taccttcctg    2100
accttaccga ttccggtggt cgcgtcaact gcatgcaggc catggacaac aacccaaaca    2160
tcaacgaatg cattccatac aactgcttga gtaacccaga agttgaagta cttggtggag    2220
aacgcattga aaccggttac actcccatcg acatctcctt gtccttgaca cagtttctgc    2280
tcagcgagtt cgtgccaggt gctgggttcg ttctcggact agttgacatc atctggggta    2340
tctttggtcc atctcaatgg gatgcattcc tggtgcaaat tgagcagttg atcaaccaga    2400
ggatcgaaga gttcgccagg aaccaggcca tctctaggtt ggaaggattg agcaatctct    2460
accaaatcta tgcagagagc ttcagagagt gggaagccga tcctactaac ccagctctcc    2520
gcgaggaaat gcgtattcaa ttcaacgaca tgaacagcgc cttgaccaca gctatcccat    2580
tgttcgcagt ccagaactac caagttcctc tcttgtccgt gtacgttcaa gcagctaatc    2640
ttcacctcag cgtgcttcga gacgttagcg tgtttgggca aaggtgggga ttcgatgctg    2700
caaccatcaa tagccgttac aacgaccta ctaggctgat tggaaactac accgaccacg    2760
ctgttcgttg gtacaacact ggcttggagc gtgtctgggg tcctgattct agagattgga    2820
ttagatacaa ccagttcagg agagaattga ccctcacagt tttggacatt gtgtctctct    2880
tcccgaacta tgactccaga acctacccta tccgtacagt gtcccaactt accagagaaa    2940
tctatactaa cccagttctt gagaacttcg acggtagctt ccgtggttct gcccaaggta    3000
tcgaaggctc catcaggagc ccacacttga tggacatctt gaacagcata actatctaca    3060
ccgatgctca cagaggagag tattactggt ctggacacca gatcatggcc tctccagttg    3120
gattcagcgg gcccgagttt accttcctc tctatggaac tatgggaaac gccgctccac    3180
aacaacgtat cgttgctcaa ctaggtcagg gtgtctacag aaccttgtct tccaccttgt    3240
acagaagacc cttcaatatc ggtatcaaca accagcaact ttccgttctt gacggaacag    3300
agttcgccta tggaacctct tctaacttgc catccgctgt ttacagaaag agcggaaccg    3360
ttgattcctt ggacgaaatc ccaccacaga acaacaatgt gccacccagg caaggattct    3420
cccacaggtt gagccacgtg tccatgttcc gttccggatt cagcaacagt tccgtgagca    3480
tcatcagagc tcctatgttc tcttggatac atcgtagtgc tgagttcaac aacatcatcg    3540
catccgatag tattactcaa atccctgcag tgaagggaaa cttttctcttc aacggttctg    3600 tcatttcagg accaggattc actggtggag acctcgttag actcaacagc agtggaaata    3660
```

```
acattcagaa tagagggtat attgaagttc caattcactt cccatccaca tctaccagat    3720
atagagttcg tgtgaggtat gcttctgtga cccctattca cctcaacgtt aattggggta    3780
attcatccat cttctccaat acagttccag ctacagctac ctccttggat aatctccaat    3840
ccagcgattt cggttacttt gaaagtgcca atgcttttac atcttcactc ggtaacatcg    3900
tgggtgttag aaactttagt gggactgcag gagtgattat cgacagattc gagttcattc    3960
cagttactgc aacactcgag gctgagtaca accttgagag agcccagaag gctgtgaacg    4020
ccctctttac ctccaccaat cagcttggct tgaaaactaa cgttactgac tatcacattg    4080
accaagtgtc caacttggtc acctacctta gcgatgagtt ctgcctcgac gagaagcgtg    4140
aactctccga gaaagttaaa cacgccaagc gtctcagcga cgagaggaat ctcttgcaag    4200
actccaactt caaagacatc aacaggcagc cagaacgtgg ttggggtgga agcaccggga    4260
tcaccatcca aggaggcgac gatgtgttca aggagaacta cgtcaccctc tccggaactt    4320
tcgacgagtg ctaccctacc tacttgtacc agaagatcga tgagtccaaa ctcaaagcct    4380
tcaccaggta tcaacttaga ggctacatcg aagacagcca agaccttgaa atctactcga    4440
tcaggtacaa tgccaagcac gagaccgtga atgtcccagg tactggttcc ctctggccac    4500
tttctgccca atctcccatt gggaagtgtg gagagcctaa cagatgcgct ccacaccttg    4560
agtggaatcc tgacttggac tgctcctgca gggatggcga gaagtgtgcc caccattctc    4620
atcacttctc cttggacatc gatgtgggat gtactgacct gaatgaggac ctcggagtct    4680
gggtcatctt caagatcaag acccaagacg gacacgcaag acttggcaac cttgagtttc    4740
tcgaagagaa accattggtc ggtgaagctc tcgctcgtgt gaagagagca gagaagaagt    4800
ggagggacaa acgtgagaaa ctcgaatggg aaactaacat cgtttacaag gaggccaaag    4860
agtccgtgga tgctttgttc gtgaactccc aatatgatca gttgcaagcc gacaccaaca    4920
tcgccatgat ccacgccgca gacaaacgtg tgcacagcat tcgtgaggct tacttgcctg    4980
agttgtccgt gatccctggt gtgaacgctg ccatcttcga ggaacttgag ggacgtatct    5040
ttaccgcatt ctccttgtac gatgccagaa acgtcatcaa gaacggtgac ttcaacaatg    5100
gcctcagctg ctggaatgtg aaaggtcatg tggacgtgga ggaacagaac aatcagcgtt    5160
ccgtcctggt tgtgcctgag tgggaagctg aagtgtccca agaggttaga gtctgtccag    5220
gtagaggcta cattctccgt gtgaccgctt acaaggaggg atacggtgag ggttgcgtga    5280
ccatccacga gatcgagaac aacaccgacg agcttaagtt ctccaactgc gtcgaggaag    5340
aaatctatcc caacaacacc gttacttgca acgactacac tgtgaatcag gaagagtacg    5400
gaggtgccta cactagccgt aacagaggtt acaacgaagc tccttccgtt cctgctgact    5460
atgcctccgt gtacgaggag aaatcctaca cagatggcag acgtgagaac ccttgcgagt    5520
tcaacagagg ttacagggac tacacaccac ttccagttgg ctatgttacc aaggagcttg    5580
agtactttcc tgagaccgac aaagtgtgga tcgagatcgg tgaaaccgag ggaaccttca    5640
tcgtggacag cgtggagctt ctcttgatgg aggaataatg agatcccgtc ctttgtcttc    5700
aattttgagg gcttttttact gaataagtat gtagtactaa aatgtatgct gtaatagctc    5760
atagtgagcg aggaaagtat cgggctattt aactatgact tgagctccat ctatgaataa    5820
ataaatcagc atatgatgct tttgttttgt gtacttcaac tgtctgctta gctaatttga    5880
tatggttggc acttggcacg tataaatatg ctgaagtaat ttactctgaa gctaaattaa    5940
ctagattaga tgagtgtatt atatacaaaa ggcattaaat cagatacatc ttagacaaat    6000
tgtcacggtc taccagaaaa gaaattgcat ttgttttttgg gtctttcaga ctgacaagat    6060
```

-continued

```
cgatctgaag tctaaacaat tctaagaggt atcatgtagc aatgtcctgc cacaatattg      6120
aattgacctg cagcccgggc ggccgcatcg atcgtgaagt ttctcatcta agcccccatt      6180
tggacgtgaa tgtagacacg tcgaaataaa gatttccgaa ttagaataat ttgtttattg      6240
ctttcgccta taaatacgac ggatcgtaat ttgtcgtttt atcaaaatgt actttcattt      6300
tataataacg ctgcggacat ctacattttt gaattgaaaa aaaattggta attactcttt      6360 cttttttctcc atattgacca tcatactcat tgctgatcca tgtagatttc ccggacatga    6420
agccat                                                                6426
```

<210> SEQ ID NO 6
<211> LENGTH: 14416
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(14416)
<223> OTHER INFORMATION: Contig of 5' flanking sequence, inserted DNA and 3' Flanking Sequence

<400> SEQUENCE: 6

```
gggaaaatcc ctcttccata ttaagaacat aaaaatcaac aggaaaaata agttcaccaa       60
cccgaaccag cacatcctct atgaaacctg cggggtaagc agcacttcta ttttccaaat      120
gaatcaccac atctgtagat tgcaaaggtc caagagataa agaattgaaa atggacagag      180
gggtgacact aactgatgct cctagatcta gcattgtatt atcaaattta ctgttcccaa      240
taatgcaagg tatacagaaa gtacctgggt ccttacattt ctcaggaatg taaggaacaa      300
atttacctat caatgctgac acatttctgc ccatgctaat cctttcattg cctttgagct      360 tcctttttgtg ggtgcacaac tcctttagaa acttgacaca tcttggaatc tgcttgatgg     420
catctagcag aggtatgttc acctctactt tcctgaaggt ctccaagatc tcctttttctg    480 cttcttccat tttttttgtt tggaattgct caaggttgga atggaagagg ataagaggc      540 tgcggtaagt cagaattact agaagaaggt ccacctgcat gaaaattttt gttaggaagc      600 tttctcttttt gtgcaactat ctcatcctct ttttcaggtg tagaatgaag cttgacaggt    660
tcaggtgcgg gtgctgctac tggtggaggt acttgaattt ggttgtcaga cctcaaggtg     720
atgacactca cattttttcgg attttgcaca gtttgtgaag gcaatttgtc agaattttgg    780
gaatgagctt ggttcaactg agtagccatc cgccccatct gatttgtcag actctgaatg    840
aaggctcttg tctcttgctg aaattgcata ttctggatgg tcatttgcct cactaactct    900
tctaaggaag gttaaggagg agtctcagtt gcttgttgtc tttgttgtga ctgttgttgt    960
tgttgctgct gtattggagg aggaacatat ggtttgcttg gaccagcaac attctggaaa   1020
ggagggacag actgttgttg ttgtgaagga cttgcccatc tcatatttgg atgatttctc   1080
caacctggat tgtatctgtt gcttggaaga tcataattat tttgctattg ttggttttgc    1140
tgttgagggg gtctattata aatgtttgca gcataagctt caggttgttc attgactcca   1200
gattactgca aagaaggaca aagatctgta tggtgatctg cagaagaaca tataccacag   1260
actcttgtaa caggtgcaaa tttctgattc atggcaagct gagttactag gttgaccaag   1320
gcatcaagtt ttccctcaag cttttattt tcagtgagata aagatgaatc tgtggccacc   1380
tcatcgactc ctctaaggac aatagcatca tttcttgcac tgaattgttg ggagttggaa   1440
gccttcttct caatcaaatt cctagcctca gcagggtca tatcacgaag agctccacca   1500
ctggcagcat caatcatact cctctccatg ttgctaagtc cctcatagaa atattgaaga   1560
```

```
aggagttgct cagaaatctg gtggtgagga cagcttgcac acaatttctt gaatctttct    1620
cagtactcat acaagctctc tccactaagt tgcctgatgc ctgaaatttc ttttctgatg    1680
gcagtggtcc tagatgcagg gaagaatttc tccaagaaca ccctcttaag gtcatcccag    1740
ctgaaaatgg acctgggagc aaggtagtag agccaatctt ttgtcactac ctccagagaa    1800
tgaggaaaag cctttagaaa gatatgatct tcttggacat caggggggctt catggtggaa    1860 caaacaatat ggaactcctt aagatgctta tgaggatctt cacctagaag accatgaaac    1920
ttgggtagca aatgtattag tccagtcttg agaacatatg gaacaccctc atcaggatat    1980
tgaatgcaca agttttcata agtgaaatca ggtgcagcca tctccctaag agtcctctca    2040
cgaggtggag gtttagccat gttctcagta tgaaaattag tagttgaatg ctcaaaatca    2100
gaatattcag aatcaccaga acaaaatac tcagaatgct caaaatgctc aaaatgcaca    2160
taatgattag gatgcacact atgcctaact aatctatgaa aggttctatc tatttcagga    2220
tcgaagggtt ataaatcacc tagattgccc ctagtcatgc actatatgta gcaaataatg    2280
tgttctcaaa caagcaccaa gggagggtta aaactacaac tatagtcaaa tgatatccaa    2340
atgagttgaa attttgtgag cagcacccta aaatcatgaa aagatagcac aaaaaatttc    2400
aaacgaaaat tcaaagtcta actatgaaaa ctacttaaga aagtttaga aaaataggac    2460 aataatactt gaaaaataaa aaaaaacata gtaaacagct gattttttcga gtttgggaga    2520 ctccaaccgg ctaaaacggg ttgccacaat atgagaaatt ttttttctacc ccaaatgcca    2580 caatatgaga agttttgct aaaatctagt tcccaaaatt tttgtctctc tcaaattcaa    2640
ccacaccaag tgctcctagt attttttcaca caaaaaatca gccaaaaata caactctaa    2700 ctatcaaaac aaaacagct aattaaattg caaaatcagt cgctaattcc tagtcactaa    2760
tcactgttca cagcaaaaca ccaactgaat cagtcgctaa acagtcgcta aacaggagac    2820
gcaactgaaa tgcaaaacag aatgctacac aaaacaaaac aactaaacac tattatgaac    2880
cttggcccca ctgctccccg acaacggcgc caaatttgat cgaggtcgta cccgaatcaa    2940
ataaacatta aaaatgcagt atctaggaag tgatcctagg tcatctccca acgagcaatg    3000
gtcaaccaat gttcataata gatagtgata aaacaataac gaattggggg ggggggtat    3060 ttgtttttgt aatttaaaca acaagcaaat tttaattaga aaataacaga attaaaacat    3120
gttatttccc cttgattcat aagcaagtct cttatcctag gttaggagga tttatcccta    3180
accagttcaa ccacttaatc caaccctaaa ttaaattact aagcgaaaat taacataagg    3240
ttgtctttat atgattaagc aacacataca ccaattaatc atgaacaaaa tcgatcatta    3300
agcatcaaca taaattaagc gcaaagataa ttaatcaagc actaagcatg catggattag    3360
tagcaacaaa tacagagtaa ttggtggaga tgaaaaactg atcaatattc aatagtaata    3420
acaaaacctc aaagagagtt gtgcttgatt ctcaagagaa acaacgctg gagacttagc    3480 cttccattaa tcagtagaaa acgaaattgt agaaaacgaa ttttattcta tgtgaacaat    3540
gtgcatgaac agtaataaaa actgaattg caaaaccca aaattattct tctctccaaa    3600
aaaactccct aaactaaaac cctggtgcta ttatataggt cctcagcccc aaagcttaca    3660
aatctatttt cagtccaaac ccataaacga aataaaataa atctggaca agataagata    3720 agattggatg aaataaaatc tggacgaaat aaaatctgga taagataaga tttgataaaa    3780
taaaattgtc tgctctttc aagtccaagc ccaattccgg attcaagccc aattttttat    3840
aattcttctg aaattaaatt aaaaatacga aattagtcaa gtaggccaa atgataaaac    3900 tgcataatta atttgacaat taaggctaat cagtaattaa aatagtgaca aaaagggtta    3960
```

```
agaaatagga gaataatgac acatcaccca tatggggagc aattctaaaa tgcatttgag   4020
ttctttaacc tgagacacag tgcagtagag tctccaagga ttcattgtgc cttttatttt   4080
atatgatggg gtcactacat tggccttgtc aaagaaactg aatttggggg attaaagaaa   4140
cacaaaataa aaacaaatga aactagttaa tagaaatgtt gcctattgct tcttggaaaa   4200
agtccaacca tttgtgattt ggataaaatt catattaccc acttgtagct tgttcaatca   4260
aacactagat ttggataaaa tctcactcct agatatacct caagggataa tatgaccaac   4320
attagtcatt tttagaaagt aaagtggaca aatttgagat tcattcctt aatgacatta    4380 taaacatgta ttttttccat gacccttttt caatgtaagt acaatttatc ccttagttta   4440
gatactctat atatgcatgt tacgtagttg atgaaaacat acctaagttg ttgtgtatgg   4500
ttaagtttgc gactacctct gatatcaaac tcctcatctc aatctcata caaaagatac     4560 ttgtcacttg gtacctgaac cttgtcagtt tgcagttgtg agtttcttct gaagccacac   4620
gcttgtatag taaccagaag ccaggaggga gtcctctaag gctctaactc gtattttccg   4680
tggaagtaca ttttttttct aaagaaaac agagatagtt taccaatgat aatatttctt    4740
tagccaaata ggaccatcat agaaaacaaa actcttcttc taagtattta atgcaactac   4800
atatttaggg tgcgtttgat tcgctaaaaa ataagggtct agacaacaca aaaatatttt   4860
tccaacgttt gattttaaaa atggctgaga gacaatacaa aataaagaat gatgaactgg   4920
acaaaaacct aaaaacttgt aactcactga atctcataca acttttttgtt cagtgtctaa  4980 aaaaagtaaa aatacaatat tattcctatt ttttactttg attatctcac accttctttc   5040
tactcatttg tttcacttca cctctccagt gggcaccttg gtttgtcggc gagagtcgta   5100
tggacttttg ttgtttcctt tttgctcatt atttctttct tttcattgtt aatttattca   5160
aatgttccca tcatcatctt actccttctt gttatgtttt ttttctttgg ccaactccaa   5220
cgaggccgtg ccgcgaccac catcatcacg accttatggc ggcctcacgc cgcaaggccc   5280
tgcacccagt ggcatcaggg gtcatgcctc cttcttaaag gtgtctctct tttgttatgt   5340
cgtcaaagtg ttgctaattc acctagaatt tttcaatgaa tcccttact tgtgggttag    5400 tctaggtcgc tctgcccggt tccaacccta gcccaaaaaa aaatgaaatg ggtaggaaag   5460
gcgggcctag tttgaattaa aataaatcat gctaagatat tgataactgc tatgtatagg   5520
tatattttgg gattaaatta tataggaatt agtaattttt ctctcttatt tcttcctttt   5580
tgttcaaata attggaattc taacatcatt taagttttta tgtagaaaat attaaaagtt   5640
gatgaattta tgatacttag tgaataatta gagtagaaaa ataaagtaaa gcccaaaaaa   5700
gaaaattggt gatatgaaga tacatgctta gcatgcccca ggcacgctta gtgtgtgtgt   5760
caaacactga tagtttaaac tgaaggcggg aaacgacaat ctgatcccca tcaagcttga   5820
tatcgaattc ctgcagcccg ggggatccac tagttctaga gcggccgcgt taactgcagg   5880
tcgacggatc cccgggtacc gagctcgaat tcaaatttat tatgtgtttt ttttccgtgg   5940
tcgagattgt gtattattct ttagttatta caagactttt agctaaaatt tgaagaattt   6000
tactttaaga aaatcttaac atctgagata atttcagcaa tagattatat ttttcattac   6060
tctagcagta tttttgcaga tcaatcgcaa catatatggt tgttagaaaa aatgcactat   6120
atatatatat attatttttt caattaaaag tgcatgatat ataatatata tatatatata   6180
tatgtgtgtg tgtatatggt caaagaaatt cttatacaaa tatacacgaa cacatatatt   6240
tgacaaaatc aaagtattac actaaacaat gagttggtgc atggccaaaa caaatatgta   6300
gattaaaaat tccagcctcc aaaaaaaaat ccaagtgttg taaagcatta tatatatata   6360
```

```
gtagatccca aattttttgta caattccaca ctgatcgaat ttttaaagtt gaatatctga    6420
cgtaggattt ttttaatgtc ttacctgacc atttactaat aacattcata cgttttcatt    6480
tgaaatatcc tctataatta tattgaattt ggcacataat aagaaaccta attggtgatt    6540
tattttacta gtaaatttct ggtgatgggc tttctactag aaagctctcg gaaaatcttg    6600
gaccaaatcc atattccatg acttcgattg ttaaccctat tagttttcac aaacatacta    6660
tcaatatcat tgcaacggaa aaggtacaag taaaacattc aatccgatag ggaagtgatg    6720
taggaggttg ggaagacagg cccagaaaga gatttatctg acttgttttg tgtatagttt    6780
tcaatgttca taaggaaga tggagacttg agaagttttt tttggacttt gtttagcttt      6840
gttgggcgtt ttttttttg atcaataact ttgttgggct tatgatttgt aatattttcg       6900
tggactcttt agtttattta gacgtgctaa ctttgttggg cttatgactt gttgtaacat    6960
attgtaacag atgacttgat gtgcgactaa tctttacaca ttaaacatag ttctgttttt     7020
tgaaagttct tattttcatt tttatttgaa tgttatatat ttttctatat ttataattct     7080
agtaaaaggc aaattttgct tttaaatgaa aaaatatat attccacagt ttcacctaat     7140
cttatgcatt tagcagtaca aattcaaaaa tttcccattt ttattcatga atcataccat    7200
tatatattaa ctaaatccaa ggtaaaaaaa aggtatgaaa gctctatagt aagtaaaata    7260
taaattcccc ataaggaaag ggccaagtcc accaggcaag taaaatgagc aagcaccact    7320
ccaccatcac acaatttcac tcatagataa cgataagatt catggaatta tcttccacgt    7380
ggcattattc cagcggttca agccgataag ggtctcaaca cctctcctta ggcctttgtg    7440
gccgttacca agtaaaatta acctcacaca tatccacact caaaatccaa cggtgtagat    7500
cctagtccac ttgaatctca tgtatcctag accctccgat cactccaaag cttgttctca    7560
ttgttgttat cattatatat agatgaccaa agcactagac caaacctcag tcacacaaag    7620
agtaaagaag aacaatggct tcctctatgc tctcttccgc tactatggtt gcctctccgg    7680
ctcaggccac tatggtcgct cctttcaacg gacttaagtc ctccgctgcc ttcccagcca    7740
cccgcaaggc taacaacgac attacttcca tcacaagcaa cggcggaaga gttaactgca    7800
tgcaggtgtg gcctccgatt ggaaagaaga agtttgagac tctctcttac cttcctgacc    7860
ttaccgattc cggtggtcgc gtcaactgca tgcaggccat ggacaacaac ccaaacatca    7920
acgaatgcat tccatacaac tgcttgagta acccagaagt tgaagtactt ggtggagaac    7980
gcattgaaac cggttacact cccatcgaca tctccttgtc cttgacacag tttctgctca    8040
gcgagttcgt gccaggtgct gggttcgttc tcggactagt tgacatcatc tggggtatct    8100
ttggtccatc tcaatgggat gcattcctgg tgcaaattga gcagttgatc aaccagagga    8160
tcgaagagtt cgccaggaac caggccatct ctaggttgga aggattgagc aatctctacc    8220
aaatctatgc agagagcttc agagagtggg aagccgatcc tactaaccca gctctccgcg    8280
aggaaatgcg tattcaattc aacgacatga acagcgcctt gaccacagct atcccattgt    8340
tcgcagtcca gaactaccaa gttcctctct tgtccgtgta cgttcaagca gctaatcttc    8400
acctcagcgt gcttcgagac gttagcgtgt ttgggcaaag gtggggattc gatgctgcaa    8460
ccatcaatag ccgttacaac gaccttacta ggctgattgg aaactacacc gaccacgctg    8520
ttcgttggta caacactggc ttggagcgtg tctggggtcc tgattctaga gattggatta    8580
gatacaacca gttcaggaga gaattgaccc tcacagtttt ggacattgtg tctctcttcc    8640
cgaactatga ctccagaacc tacccctatcc gtacagtgtc ccaacttacc agagaaatct    8700
atactaaccc agttcttgag aacttcgacg gtagcttccg tggttctgcc caaggtatcg    8760
```

```
aaggctccat caggagccca cacttgatgg acatcttgaa cagcataact atctacaccg   8820
atgctcacag aggagagtat tactggtctg acaccagat catggcctct ccagttggat    8880
tcagcgggcc cgagtttacc tttcctctct atggaactat gggaaacgcc gctccacaac   8940
aacgtatcgt tgctcaacta ggtcagggtg tctacagaac cttgtcttcc accttgtaca   9000 gaagacccttt caatatcggt atcaacaacc agcaactttc cgttcttgac ggaacagagt  9060
tcgcctatgg aacctcttct aacttgccat ccgctgttta cagaaagagc ggaaccgttg   9120
attccttgga cgaaatccca ccacagaaca acaatgtgcc acccaggcaa ggattctccc   9180
acaggttgag ccacgtgtcc atgttccgtt ccggattcag caacagttcc gtgagcatca   9240
tcagagctcc tatgttctct tggatacatc gtagtgctga gttcaacaac atcatcgcat   9300
ccgatagtat tactcaaatc cctgcagtga agggaaactt tctcttcaac ggttctgtca   9360
tttcaggacc aggattcact ggtggagacc tcgttagact caacagcagt ggaaataaca   9420
ttcagaatag agggtatatt gaagttccaa ttcacttccc atccacatct accagatata   9480
gagttcgtgt gaggtatgct tctgtgaccc ctattcacct caacgttaat tggggtaatt   9540
catccatctt ctccaataca gttccagcta cagctacctc cttggataat ctccaatcca   9600
gcgatttcgg ttactttgaa agtgccaatg cttttacatc ttcactcggt aacatcgtgg   9660
gtgttagaaa ctttagtggg actgcaggag tgattatcga cagattcgag ttcattccag   9720
ttactgcaac actcgaggct gagtacaacc ttgagagagc ccagaaggct gtgaacgccc   9780
tctttacctc caccaatcag cttggcttga aaactaacgt tactgactat cacattgacc   9840
aagtgtccaa cttggtcacc taccttagcg atgagttctg cctcgacgag aagcgtgaac   9900
tctccgagaa agtaaacac gccaagcgtc tcagcgacga gggaatctc ttgcaagact    9960 ccaacttcaa agacatcaac aggcagccag aacgtggttg gggtggaagc accgggatca  10020
ccatccaagg aggcgacgat gtgttcaagg agaactacgt caccctctcc ggaactttcg  10080
acgagtgcta ccctacctac ttgtaccaga agatcgatga gtccaaactc aaagccttca  10140
ccaggtatca acttagaggc tacatcgaag acagccaaga ccttgaaatc tactcgatca  10200
ggtacaatgc caagcacgag accgtgaatg tcccaggtac tggttccctc tggccacttt  10260
ctgcccaatc tcccattggg aagtgtggag agcctaacag atgcgctcca caccttgagt  10320
ggaatcctga cttggactgc tcctgcaggg atggcgagaa gtgtgcccac cattctcatc  10380
acttctcctt ggacatcgat gtgggatgta ctgacctgaa tgaggacctc ggagtctggg  10440
tcatcttcaa gatcaagacc caagacggac acgcaagact tggcaacctt gagtttctcg  10500
aagagaaacc attggtcggt gaagctctcg ctcgtgtgaa gagagcagag aagaagtgga  10560
gggacaaacg tgagaaactc gaatgggaaa ctaacatcgt ttacaaggag gccaaagagt  10620
ccgtggatgc tttgttcgtg aactcccaat atgatcagtt gcaagccgac accaacatcg  10680
ccatgatcca cgccgcagac aaacgtgtgc acagcattcg tgaggcttac ttgcctgagt  10740
tgtccgtgat ccctggtgtg aacgctgcca tcttcgagga acttgaggga cgtatcttta  10800
ccgcattctc cttgtacgat gccagaaacg tcatcaagaa cggtgacttc aacaatggcc  10860
tcagctgctg gaatgtgaaa ggtcatgtgg acgtggagga acagaacaat cagcgttccg  10920
tcctggttgt gcctgagtgg gaagctgaag tgtcccaaga ggttagagtc tgtccaggta  10980
gaggctacat tctccgtgtg accgcttaca aggagggata cggtgagggt tgcgtgacca  11040
tccacgagat cgagaacaac accgacgagc ttaagttctc caactgcgtc gaggaagaaa  11100
tctatcccaa caacaccgtt acttgcaacg actacactgt gaatcaggaa gagtacggag  11160
```

```
gtgcctacac tagccgtaac agaggttaca acgaagctcc ttccgttcct gctgactatg    11220
cctccgtgta cgaggagaaa tcctacacag atggcagacg tgagaaccct tgcgagttca    11280
acagaggtta cagggactac acaccacttc cagttggcta tgttaccaag gagcttgagt    11340
actttcctga gaccgacaaa gtgtggatcg agatcggtga aaccgaggga accttcatcg    11400
tggacagcgt ggagcttctc ttgatggagg aataatgaga tcccgtcctt tgtcttcaat    11460
tttgagggct ttttactgaa taagtatgta gtactaaaat gtatgctgta atagctcata    11520
gtgagcgagg aaagtatcgg gctatttaac tatgacttga gctccatcta tgaataaata    11580
aatcagcata tgatgctttt gttttgtgta cttcaactgt ctgcttagct aatttgatat    11640
ggttggcact tggcacgtat aaatatgctg aagtaattta ctctgaagct aaattaacta    11700
gattagatga gtgtattata tacaaaaggc attaaatcag atacatctta gacaaattgt    11760
cacggtctac cagaaaagaa attgcatttg ttttgggtc tttcagactg acaagatcga    11820
tctgaagtct aaacaattct aagaggtatc atgtagcaat gtcctgccac aatattgaat    11880
tgacctgcag cccgggcggc cgcatcgatc gtgaagtttc tcatctaagc ccccatttgg    11940
acgtgaatgt agacacgtcg aaataaagat ttccgaatta gaataatttg tttattgctt    12000
tcgcctataa atacgacgga tcgtaatttg tcgttttatc aaaatgtact ttcattttat    12060
aataacgctg cggacatcta cattttgaa ttgaaaaaa attggtaatt actctttctt    12120
tttctccata ttgaccatca tactcattgc tgatccatgt agatttcccg gacatgaagc    12180
catcaaaaag taggactaat ttaggaaagc aagctaattc aagaaagtga aggcacgctt    12240
agtgtgagac acgtgttgag cgcgattact gccactcact aaccacacaa gtgcactcag    12300
tgcgaaggtt gcttaaaaat taagttgatt cgcacttata aagaaggat agagatgaag    12360
gaaaaaacac agaaaataca attccttata gaagacaaag gctagaagaa gcaaacgcaa    12420
acattagaag tcattccttc cctcaattcc ctttttcaat ttccccttt actaaatatt    12480
ctcctcttgc aattataaag cctcctatga caatgacaag ctaaactctc ctttgttggg    12540
aacttatcag tcaactgctc ttaatataat ttctcttcct atctattatg aatattcact    12600
acaagaaata tgcccatttg ccagggattt ttgacaggga cattacccccc tggcaaattt    12660
cccagggact aagccaagga aaccctggc aaaatgacat ttgagaaggc tgggaccact    12720
tacatttaca caggggtttg tccctcgcaa aaatacaaaa gccttggcaa aaaaaagagc    12780
gggaaatgaa ttttaaaaca gcatgttgtt ttcacacagc caaacacacg ggtatgccct    12840
cgttttctgt aaagctgacg gaatcttccc ataagtcaac acgacatgac catgcactgc    12900
aaaaagctgt gcggcccaga cgtgacaggg gtgttacccc tcggaaatgg cttgcagccc    12960
ctggcaaaaa ggaatccctg ctttcctagc tacaccgttc tgctcatata gctgaagcta    13020
ggaggttagc ctttgactct gttgttttgc gagggcatt ccgtgagtta ttccctgggt    13080
ttttttacac tatatagcca aaccgcgtgt ttatcctcat gctcagtgtt gtgttttga    13140
aacttagaaa aattttcggt ttccatttcc atcctcacca gttcattttc agtccattat    13200
cattcagttc atacacttgt tctataattt ggtaacactc ttttcactta ttatattttt    13260
ctgtttttat ttgttactac ttattaacat aaatattttt tattgtatca gtgtccaaat    13320
ttgcctcctc ctgctgctcc ttgctctctg aatttgttct cttaagcttc aacaagttag    13380
taattttttct acttataatt ttagatatat gatgtttata tatatgatgt tataattttg    13440
catgatctgt caaagaaaat atgatgtttc tacttgcatg atgtgttata atatatgatg    13500
tttatatata tttcgaattt tgttgttaat aaaactgttt aattagaaac tgtataattt    13560
```

-continued

```
ttttgtttaa taaaactgtt taattttgca tgatctgttt aataaaactg tttatataaa   13620
actgtttata tataatatat gatgttaaca tttttaaaac tgtttataaa acagtttagt   13680
tagaaaaaat gttaaaacta gagaaaaaaa tgtataataa aactgtgtca gtacagcagc   13740
gcgtcagaaa agtgtgcaga tgcgtcagtg agaagacagg ggctaagaca gggattttga   13800
cagggaattt tgccagggat tttgccaggg tcagcccctc gttttttttgc caggggtgaa   13860 atccctggca aactgatttg cgatgggcgt ttttcccagg gattcagccc ctggcaaaat   13920
ccctggcaaa cgtccatttc ccagggcttt tgttcttttt cccagggaat ccgcccctgg   13980
caaacgagct tgtttcttgt agtgattact tttgcattag ttttttcctgt atttaattttt   14040 attgtttatg gcttgattac ccatttgcat tataagttt aggggtagcg ttgaaaagtg   14100
ttattctcta atagaactgg aaaagagtat ttaaataact tcatcactag ggatacattg   14160
attttattta gcttattata tatctctatt attaatgtaa tttaactatt ttatctctgc   14220
aaagtgattt gggagagaag atagataagt tagactcttt cactcgaggc tgagtacaac   14280
cttgagagag cccagaaggc tgtgaacgcc ctctttacct ccaccaatca gcttggcttg   14340
aaaactaacg ttactgacta tcacattgac caagtgtcca acttggtcac ctaccttagc   14400
gatgagttct gaaggg                                                    14416
```

<210> SEQ ID NO 7
<211> LENGTH: 6916
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(6916)
<223> OTHER INFORMATION: TIC107 expression cassette with full right and left borders

<400> SEQUENCE: 7

```
aggatttttc ggcgctgcgc tacgtccgcg accgcgttga gggatcaagc cacagcagcc      60
cactcgacct tctagccgac ccagacgagc caagggatct ttttggaatg ctgctccgtc     120
gtcaggcttt ccgacgtttg ggtggttgaa cagaagtcat tatcgcacgg aatgccaagc     180
actcccgagg ggaaccctgt ggttggcatg cacatacaaa tggacgaacg gataaacctt     240
ttcacgccct tttaaatatc cgattattct aataaacgct cttttctctt aggtttaccc     300
gccaatatat cctgtcaaac actgatagtt taaactgaag gcgggaaacg acaatctgat     360
ccccatcaag cttgatatcg aattcctgca gcccggggga tccactagtt ctagagcggc     420
cgcgttaact gcaggtcgac ggatccccgg gtaccgagct cgaattcaaa ttttattatgt    480 gttttttttc cgtggtcgag attgtgtatt attctttagt tattacaaga cttttagcta    540
aaatttgaaa gaatttactt taagaaaatc ttaacatctg agataatttc agcaatagat     600
tatatttttc attactctag cagtattttt gcagatcaat cgcaacatat atggttgtta     660
gaaaaaatgc actatatata tatatattat tttttcaatt aaaagtgcat gatatataat     720
atatatatat atatatatgt gtgtgtgtat atggtcaaag aaattcttat acaaatatac     780
acgaacacat atatttgaca aaatcaaagt attacactaa acaatgagtt ggtgcatggc     840
caaaacaaat atgtagatta aaaattccag cctccaaaaa aaatccaag tgttgtaaag     900 cattatatat atatagtaga tcccaaattt ttgtacaatt ccacactgat cgaattttta     960
aagttgaata tctgacgtag gatttttttta atgtcttacc tgaccatttta ctaataacat   1020
```

```
tcatacgttt tcatttgaaa tatcctctat aattatattg aatttggcac ataataagaa    1080
acctaattgg tgatttattt tactagtaaa tttctggtga tgggctttct actagaaagc    1140
tctcggaaaa tcttggacca atccatatt ccatgacttc gattgttaac cctattagtt    1200
ttcacaaaca tactatcaat atcattgcaa cggaaaaggt acaagtaaaa cattcaatcc    1260
gatagggaag tgatgtagga ggttgggaag acaggcccag aaagagattt atctgacttg    1320
ttttgtgtat agttttcaat gttcataaag gaagatggag acttgagaag tttttttttgg   1380 actttgttta gctttgttgg gcgttttttt ttttgatcaa taactttgtt gggcttatga    1440
tttgtaatat tttcgtggac tctttagttt atttagacgt gctaactttg ttgggcttat    1500
gacttgttgt aacatattgt aacagatgac ttgatgtgcg actaatcttt acacattaaa    1560
catagttctg tttttttgaaa gttcttattt tcatttttat ttgaatgtta tatattttttc   1620 tatatttata attctagtaa aaggcaaatt ttgcttttaa atgaaaaaaa tatatattcc    1680
acagtttcac ctaatcttat gcatttagca gtacaaattc aaaaatttcc cattttttatt   1740 catgaatcat accattatat attaactaaa tccaaggtaa aaaaaaggta tgaaagctct    1800
atagtaagta aaatataaat tccccataag gaaagggcca agtccaccag gcaagtaaaa    1860
tgagcaagca ccactccacc atcacacaat ttcactcata gataacgata agattcatgg    1920
aattatcttc cacgtggcat tattccagcg gttcaagccg ataagggtct caacacctct    1980
ccttaggcct ttgtggccgt taccaagtaa aattaacctc acacatatcc acactcaaaa    2040
tccaacggtg tagatcctag tccacttgaa tctcatgtat cctagaccct ccgatcactc    2100
caaagcttgt tctcattgtt gttatcatta tatatagatg accaaagcac tagaccaaac    2160
ctcagtcaca caaagagtaa agaagaacaa tggcttcctc tatgctctct tccgctacta    2220
tggttgcctc tccggctcag gccactatgg tcgctccttt caacggactt aagtcctccg    2280
ctgccttccc agccaccccgc aaggctaaca acgacattac ttccatcaca agcaacggcg    2340
gaagagttaa ctgcatgcag gtgtggcctc cgattggaaa gaagaagttt gagactctct    2400
cttaccttcc tgaccttacc gattccggtg tcgcgtcaa ctgcatgcag gccatggaca    2460
acaacccaaa catcaacgaa tgcattccat acaactgctt gagtaaccca gaagttgaag    2520
tacttggtgg agaacgcatt gaaaccggtt acactcccat cgacatctcc ttgtccttga    2580
cacagtttct gctcagcgag ttcgtgccag gtgctgggtt cgttctcgga ctagttgaca    2640
tcatctgggg tatctttggt ccatctcaat gggatgcatt cctggtgcaa attgagcagt    2700
tgatcaacca gaggatcgaa gagttcgcca ggaaccaggc catctctagg ttggaaggat    2760
tgagcaatct ctaccaaatc tatgcagaga gcttcagaga gtgggaagcc gatcctacta    2820
acccagctct ccgcgaggaa atgcgtattc aattcaacga catgaacagc gccttgacca    2880
cagctatccc attgttcgca gtccagaact accaagttcc tctcttgtcc gtgtacgttc    2940
aagcagctaa tcttcacctc agcgtgcttc gagacgttag cgtgtttggg caaaggtggg    3000
gattcgatgc tgcaaccatc aatagccgtt acaacgacct tactaggctg attggaaact    3060
acaccgacca cgctgttcgt tggtacaaca ctggcttgga gcgtgtctgg ggtcctgatt    3120
ctagagattg gattagatac aaccagttca ggagagaatt gaccctcaca gttttggaca    3180
ttgtgtctct cttcccgaac tatgactcca gaacctaccc tatccgtaca gtgtcccaac    3240
ttaccagaga aatctatact aacccagttc ttgagaactt cgacggtagc ttccgtggtt    3300
ctgcccaagg tatcgaaggc tccatcagga gcccacactt gatggacatc ttgaacagca    3360
taactatcta caccgatgct cacagaggag agtattactg gtctggacac cagatcatgg    3420
```

```
cctctccagt tggattcagc gggcccgagt ttacctttcc tctctatgga actatgggaa      3480
acgccgctcc acaacaacgt atcgttgctc aactaggtca gggtgtctac agaaccttgt      3540
cttccacctt gtacagaaga cccttcaata tcggtatcaa caaccagcaa ctttccgttc      3600
ttgacggaac agagttcgcc tatggaacct cttctaactt gccatccgct gtttacagaa      3660
agagcggaac cgttgattcc ttggacgaaa tcccaccaca gaacaacaat gtgccaccca      3720
ggcaaggatt ctcccacagg ttgagccacg tgtccatgtt ccgttccgga ttcagcaaca      3780
gttccgtgag catcatcaga gctcctatgt tctcttggat acatcgtagt gctgagttca      3840
acaacatcat cgcatccgat agtattactc aaatccctgc agtgaaggga aactttctct      3900
tcaacggttc tgtcatttca ggaccaggat tcactggtgg agacctcgtt agactcaaca      3960
gcagtggaaa taacattcag aatagagggt atattgaagt tccaattcac ttcccatcca      4020
catctaccag atatagagtt cgtgtgaggt atgcttctgt gacccctatt cacctcaacg      4080
ttaattgggg taattcatcc atcttctcca atacagttcc agctacagct acctccttgg      4140
ataatctcca atccagcgat ttcggttact ttgaaagtgc aatgcttttt acatcttcac      4200
tcggtaacat cgtgggtgtt agaaacttta gtgggactgc aggagtgatt atcgacagat      4260
tcgagttcat tccagttact gcaacactcg aggctgagta caaccttgag agagcccaga      4320
aggctgtgaa cgccctcttt acctccacca atcagcttgg cttgaaaact aacgttactg      4380
actatcacat tgaccaagtg tccaacttgg tcacctacct tagcgatgag ttctgcctcg      4440
acgagaagcg tgaactctcc gagaaagtta aacacgccaa cgtctcagc gacgagagga      4500 atctcttgca agactccaac ttcaaagaca tcaacaggca gccagaacgt ggttggggtg      4560
gaagcaccgg gatcaccatc caaggaggcg acgatgtgtt caaggagaac tacgtcaccc      4620
tctccggaac tttcgacgag tgctacccta cctacttgta ccagaagatc gatgagtcca      4680
aactcaaagc cttcaccagg tatcaactta gaggctacat cgaagacagc caagaccttg      4740
aaatctactc gatcaggtac aatgccaagc acgagaccgt gaatgtccca ggtactggtt      4800
ccctctggcc acttttctgcc caatctccca ttgggaagtg tggagagcct aacagatgcg      4860
ctccacacct tgagtggaat cctgacttgg actgctcctg cagggatggc gagaagtgtg      4920
cccaccattc tcatcacttc tccttggaca tcgatgtggg atgtactgac ctgaatgagg      4980
acctcggagt ctgggtcatc ttcaagatca agacccaaga cggacacgca agacttggca      5040
accttgagtt tctcgaagag aaaccattgg tcggtgaagc tctcgctcgt gtgaagagag      5100
cagagaagaa gtgagggac aaacgtgaga aactcgaatg gaaactaac atcgtttaca      5160 aggaggccaa agagtccgtg gatgctttgt tcgtgaactc ccaatatgat cagttgcaag      5220
ccgacaccaa catcgccatg atccacgccg cagacaaacg tgtgcacagc attcgtgagg      5280
cttacttgcc tgagttgtcc gtgatccctg gtgtgaacgc tgccatcttc gaggaacttg      5340
agggacgtat ctttaccgca ttctccttgt acgatgccag aaacgtcatc aagaacggtg      5400
acttcaacaa tggcctcagc tgctggaatg tgaaaggtca tgtggacgtg gaggaacaga      5460
acaatcagcg ttccgtcctg gttgtgcctg agtgggaagc tgaagtgtcc caagaggtta      5520
gagtctgtcc aggtagaggc tacattctcc gtgtgaccgc ttacaaggag ggatacggtg      5580
agggttgcgt gaccatccac gagatcgaga acaacaccga cgagcttaag ttctccaact      5640
gcgtcgagga agaaatctat cccaacaaca ccgttacttg caacgactac actgtgaatc      5700
aggaagagta cggaggtgcc tacactagcc gtaacgagg ttacaacgaa gctccttccg      5760
ttcctgctga ctatgcctcc gtgtacgagg agaaatccta cacagatggc agacgtgaga      5820
```

-continued

```
acccttgcga gttcaacaga ggttacaggg actacacacc acttccagtt ggctatgtta    5880
ccaaggagct tgagtacttt cctgagaccg acaaagtgtg gatcgagatc ggtgaaaccg    5940
agggaacctt catcgtggac agcgtggagc ttctcttgat ggaggaataa tgagatcccg    6000
tcctttgtct tcaattttga gggcttttta ctgaataagt atgtagtact aaaatgtatg    6060
ctgtaatagc tcatagtgag cgaggaaagt atcgggctat ttaactatga cttgagctcc    6120
atctatgaat aaataaatca gcatatgatg cttttgtttt gtgtacttca actgtctgct    6180
tagctaattt gatatggttg gcacttggca cgtataaata tgctgaagta atttactctg    6240
aagctaaatt aactagatta gatgagtgta ttatatacaa aaggcattaa atcagataca    6300
tcttagacaa attgtcacgg tctaccagaa aagaaattgc atttgttttt gggtctttca    6360
gactgacaag atcgatctga agtctaaaca attctaagag gtatcatgta gcaatgtcct    6420
gccacaatat tgaattgacc tgcagcccgg gcggccgcat cgatcgtgaa gtttctcatc    6480
taagccccca tttggacgtg aatgtagaca cgtcgaaata aagatttccg aattagaata    6540
atttgtttat tgctttcgcc tataaatacg acggatcgta atttgtcgtt ttatcaaaat    6600
gtactttcat tttataataa cgctgcggac atctacattt ttgaattgaa aaaaaattgg    6660
taattactct ttcttttttct ccatattgac catcatactc attgctgatc catgtagatt    6720
tcccggacat gaagccattt acaattgaat atatcctgcc gccgctgccg ctttgcaccc    6780
ggtggagctt gcatgttggt ttctacgcag aactgagccg gttaggcaga taatttccat    6840
tgagaactga gccatgtgca ccttcccccc aacacggtga gcgacggggc aacggagtga    6900
tccacatggg actttt                                                   6916
```

<210> SEQ ID NO 8
<211> LENGTH: 3801
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(3801)
<223> OTHER INFORMATION: DNA encoding the TIC107 insect toxin including the chlorplast transit peptide encoding sequence

<400> SEQUENCE: 8

```
atggcttcct ctatgctctc ttccgctact atggttgcct ctccggctca ggccactatg     60
gtcgctcctt tcaacggact taagtcctcc gctgccttcc cagccacccg caaggctaac    120
aacgacatta cttccatcac aagcaacggc ggaagagtta actgcatgca ggtgtggcct    180
ccgattggaa agaagaagtt tgagactctc tcttaccttc ctgacttac cgattccggt    240 ggtcgcgtca actgcatgca ggccatggac aacaacccaa acatcaacga atgcattcca    300
tacaactgct tgagtaaccc agaagttgaa gtacttggtg agaacgcat tgaaaccggt    360 tacactccca tcgacatctc cttgtccttg acacagtttc tgctcagcga gttcgtgcca    420
ggtgctgggt tcgttctcgg actagttgac atcatctggg gtatctttgg tccatctcaa    480
tgggatgcat tcctggtgca aattgagcag ttgatcaacc agaggatcga agagttcgcc    540
aggaaccagg ccatctctag gttggaagga ttgagcaatc tctaccaaat ctatgcagag    600
agcttcagag agtgggaagc cgatcctact aacccagctc tccgcgagga aatgcgtatt    660
caattcaacg acatgaacag cgccttgacc acagctatcc cattgttcgc agtccagaac    720
taccaagttc ctctcttgtc cgtgtacgtt caagcagcta atcttcacct cagcgtgctt    780
cgagacgtta gcgtgtttgg gcaaaggtgg ggattcgatg ctgcaaccat caatagccgt    840
```

```
tacaacgacc ttactaggct gattggaaac tacaccgacc acgctgttcg ttggtacaac      900
actggcttgg agcgtgtctg gggtcctgat tctagagatt ggattagata caaccagttc      960
aggagagaat tgaccctcac agttttggac attgtgtctc tcttcccgaa ctatgactcc     1020
agaacctacc ctatccgtac agtgtcccaa cttaccagag aaatctatac taacccagtt     1080
cttgagaact tcgacggtag cttccgtggt tctgcccaag gtatcgaagg ctccatcagg     1140
agcccacact tgatggacat cttgaacagc ataactatct acaccgatgc tcacagagga     1200
gagtattact ggtctggaca ccagatcatg gcctctccag ttggattcag cgggcccgag     1260
tttacctttc ctctctatgg aactatggga aacgccgctc cacaacaacg tatcgttgct     1320
caactaggtc agggtgtcta cagaaccttg tcttccacct tgtacagaag accttcaat    1380 atcggtatca acaaccagca actttccgtt cttgacggaa cagagttcgc ctatggaacc     1440
tcttctaact tgccatccgc tgtttacaga aagagcggaa ccgttgattc cttggacgaa     1500
atcccaccac agaacaacaa tgtgccaccc aggcaaggat tctcccacag gttgagccac     1560
gtgtccatgt tccgttccgg attcagcaac agttccgtga gcatcatcag agctcctatg     1620
ttctcttgga tacatcgtag tgctgagttc aacaacatca tcgcatccga tagtattact     1680
caaatccctg cagtgaaggg aaactttctc ttcaacggtt ctgtcatttc aggaccagga     1740
ttcactggtg gagacctcgt tagactcaac agcagtggaa ataacattca gaatagaggg     1800
tatattgaag ttccaattca cttcccatcc acatctacca gatatagagt tcgtgtgagg     1860
tatgcttctg tgaccctat tcacctcaac gttaattggg gtaattcatc catcttctcc      1920
aatacagttc cagctacagc tacctccttg gataatctcc aatccagcga tttcggttac     1980
tttgaaagtg ccaatgcttt tacatcttca ctcggtaaca tcgtgggtgt tagaaacttt     2040
agtgggactg caggagtgat tatcgacaga ttcgagttca ttccagttac tgcaacactc     2100
gaggctgagt acaaccttga gagagcccag aaggctgtga acgccctctt tacctccacc     2160
aatcagcttg gcttgaaaac taacgttact gactatcaca ttgaccaagt gtccaacttg     2220
gtcacctacc ttagcgatga gttctgcctc gacgagaagc gtgaactctc cgagaaagtt     2280
aaacacgcca gcgtctcag cgacgagagg aatctcttgc aagactccaa cttcaaagac     2340
atcaacaggc agccagaacg tggttggggt ggaagcaccg ggatcaccat ccaaggaggc     2400
gacgatgtgt tcaaggagaa ctacgtcacc ctctccggaa ctttcgacga gtgctaccct     2460
acctacttgt accagaagat cgatgagtcc aaactcaaag ccttcaccag gtatcaactt     2520
agaggctaca tcgaagacag ccaagacctt gaaatctact cgatcaggta caatgccaag     2580
cacgagaccg tgaatgtccc aggtactggt tccctctggc cactttctgc ccaatctccc     2640
attgggaagt gtggagagcc taacagatgc gctccacacc ttgagtggaa tcctgacttg     2700
gactgctcct gcagggatgg cgagaagtgt gcccaccatt tcatcacttt ctccttggac     2760
atcgatgtgg gatgtactga cctgaatgag gacctcggag tctgggtcat cttcaagatc     2820
aagacccaag acggacacgc aagacttggc aaccttgagt ttctcgaaga gaaaccattg     2880
gtcggtgaag ctctcgctcg tgtgaagaga gcagagaaga gtggaggga caaacgtgag     2940 aaactcgaat gggaaactaa catcgtttac aaggaggcca agagtccgt ggatgctttg      3000 ttcgtgaact cccaatatga tcagttcaa gccgacacca catcgccat gatccacgcc      3060 gcagacaaac gtgtgcacag cattcgtgag gcttacttgc ctgagttgtc cgtgatccct     3120
ggtgtgaacg ctgccatctt cgaggaactt gagggacgta tctttaccgc attctccttg     3180
tacgatgcca gaaacgtcat caagaacggt gacttcaaca atggcctcag ctgctggaat     3240
```

```
gtgaaaggtc atgtggacgt ggaggaacag aacaatcagc gttccgtcct ggttgtgcct    3300
gagtgggaag ctgaagtgtc ccaagaggtt agagtctgtc caggtagagg ctacattctc    3360
cgtgtgaccg cttacaagga gggatacggt gagggttgcg tgaccatcca cgagatcgag    3420
aacaacaccg acgagcttaa gttctccaac tgcgtcgagg aagaaatcta tcccaacaac    3480
accgttactt gcaacgacta cactgtgaat caggaagagt acggaggtgc ctacactagc    3540
cgtaacagag gttacaacga agctccttcc gttcctgctg actatgcctc cgtgtacgag    3600
gagaaatcct acacagatgg cagacgtgag aaccccttgcg agttcaacag aggttacagg    3660
gactacacac cacttccagt tggctatgtt accaaggagc ttgagtactt tcctgagacc    3720
gacaaagtgt ggatcgagat cggtgaaacc gagggaacct tcatcgtgga cagcgtggag    3780
cttctcttga tggaggaata a                                              3801
```

<210> SEQ ID NO 9
<211> LENGTH: 25
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(25)
<223> OTHER INFORMATION: oligonucleotide primer SQ1135

<400> SEQUENCE: 9

```
cccgccttca gtttaaacta tcagt                                          25
```

<210> SEQ ID NO 10
<211> LENGTH: 28
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: Oligonucleotide primer SQ1136

<400> SEQUENCE: 10

```
attggtgata tgaagataca tgcttagc                                       28
```

<210> SEQ ID NO 11
<211> LENGTH: 16
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(16)
<223> OTHER INFORMATION: 6FAM-labeled oligonucleotide probe PB63

<400> SEQUENCE: 11

```
ttgacacaca cactaa                                                    16
```

<210> SEQ ID NO 12
<211> LENGTH: 24
<212> TYPE: DNA
<213> ORGANISM: Artificial sequence
<220> FEATURE:

```
<223> OTHER INFORMATION: Synthetic
<220> FEATURE:
<221> NAME/KEY: misc_feature
<222> LOCATION: (1)..(24)
<223> OTHER INFORMATION: Oligonucleotide primer SQ3443

<400> SEQUENCE: 12
cattgctgat ccatgtagat ttcc                                              24

<210> SEQ ID NO 13
<211> LENGTH: 28
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(28)
<223> OTHER INFORMATION: Oligonucleotide primer SQ3445

<400> SEQUENCE: 13
agcttgcttt cctaaattag tcctactt                                          28

<210> SEQ ID NO 14
<211> LENGTH: 18
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(18)
<223> OTHER INFORMATION: Oligonucleotide primer SQ3446

<400> SEQUENCE: 14
ggcgctctgc acgatgta                                                     18

<210> SEQ ID NO 15
<211> LENGTH: 16
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(16)
<223> OTHER INFORMATION: 6FAM-labeled oligonucleotide probe PB1111

<400> SEQUENCE: 15
acatgaagcc atcaaa                                                       16

<210> SEQ ID NO 16
<211> LENGTH: 14
<212> TYPE: DNA
<213> ORGANISM: Artificial sequence
<220> FEATURE:
<223> OTHER INFORMATION: Synthetic
<220> FEATURE:
<221> NAME/KEY: misc_feature
<222> LOCATION: (1)..(14)
<223> OTHER INFORMATION: VIC-labeled oligonucleotide probe PB1112

<400> SEQUENCE: 16
aggctcagtg gcgc                                                         14
```

SOYBEAN PLANT AND SEED CORRESPONDING TO TRANSGENIC EVENT MON87701 AND METHODS FOR DETECTION THEREOF

This application claims the benefit of priority to U.S. Provisional Application Ser. No. 60/988,349, filed Nov. 15, 2007, which is herein incorporated by reference in its entirety.

FIELD OF THE INVENTION

The present invention relates to transgenic soybean event MON87701 and plant parts and seed thereof. The event exhibits resistance to insect infestation from insects in the order of Lepidoptera. The present invention also relates to methods for detecting the presence of said soybean event in a biological sample, and provides nucleotide sequences that are unique to the event.

BACKGROUND OF THE INVENTION

Soybean is an important crop and is a primary food source in many areas of the world. The methods of biotechnology have been applied to soybean for improvement of agronomic traits and the quality of the product. One such agronomic trait is insect resistance.

It would be advantageous to be able to detect the presence of transgene/genomic DNA of a particular plant in order to determine whether progeny of a sexual cross contain the transgene/genomic DNA of interest. In addition, a method for detecting a particular plant would be helpful when complying with regulations requiring the pre-market approval and labeling of foods derived from the recombinant crop plants.

Transgenic crops expressing *B. thuringiensis* δ-endotoxins enable growers to significantly reduce the time and cost associated with applying chemical insecticides as well as increase crop yields in transgenic plants grown under heavy insect pressure as compared to greatly reduced yields in non-transgenic commercial plant varieties. Despite this success, it is still anticipated that insects may evolve resistance to *B. thuringiensis* δ-endotoxins expressed in transgenic plants. Such resistance, should it become widespread, would clearly limit the commercial value of germplasm containing genes encoding some *B. thuringiensis* δ-endotoxins.

One possible way of increasing the effectiveness of the transgenic insecticides against target pests and contemporaneously reducing the development of insecticide-resistant pests would be to ensure that transgenic crops express high levels of *B. thuringiensis* δ-endotoxins (McGaughey and Whalon (1992), Science 258:1451-55; Roush Roush (1994), Biocontrol. Sci. Technol. 4:501-516). Of the many insecticidal proteins identified from *Bacillus thuringiensis*, relatively few individual insecticidal proteins such as Cry1's, Cry3's, VIP3A, Cry34, Cry35 and Cry2Ab have been tested for expression in plants. In the case of Cry2Ab, in order to achieve high levels of in planta expression, this insecticidal protein (Cry2Ab) had to be targeted to the chloroplast to avoid undesirable phytotoxic effects.

The expression of foreign genes in plants is known to be influenced by their chromosomal position, perhaps due to chromatin structure (e.g., heterochromatin) or the proximity of transcriptional regulation elements (e.g., enhancers) close to the integration site (Weising et al. (1988), Ann. Rev. Genet 22:421-477). For this reason, it is often necessary to screen a large number of events in order to identify an event characterized by optimal expression of an introduced gene of interest. For example, it has been observed in plants and in other organisms that there may be wide variation in the levels of expression of an introduced gene among events. There may also be differences in spatial or temporal patterns of expression, for example, differences in the relative expression of a transgene in various plant tissues, that may not correspond to the patterns expected from transcriptional regulatory elements present in the introduced gene construct. For this reason, it is common to produce several hundreds to several thousands different events and screen the events for a single event that has the desired transgene expression levels and patterns for commercial purposes. An event that has the desired levels or patterns of transgene expression is useful for introgressing the transgene into other genetic backgrounds by sexual outcrossing using conventional breeding methods. Progeny of such crosses maintain the transgene expression characteristics of the original transformant. This strategy is used to ensure reliable gene expression in a number of varieties that are suitably adapted to specific local growing conditions.

It is possible to detect the presence of a transgene by any well known nucleic acid detection method such as the polymerase chain reaction (PCR) or DNA hybridization using nucleic acid probes. These detection methods generally focus on frequently used genetic elements, such as promoters, terminators, marker genes, etc. As a result, such methods may not be useful for discriminating between different events, particularly those produced using the same DNA construct unless the sequence of chromosomal DNA adjacent to the inserted DNA ("flanking DNA") is known. An event-specific PCR assay is discussed, for example, by Taverniers et al. (J. Agric. Food Chem., 53: 3041-3052, 2005) in which an event-specific tracing system for transgenic maize lines Bt11, Bt176, and GA21 and for canola event GT73 is demonstrated. In this study, event-specific primers and probes were designed based upon the sequences of the genome/transgene junctions for each event. Transgenic plant event specific DNA detection methods have also been described in U.S. Pat. Nos. 6,893,826; 6,825,400; 6,740,488; 6,733,974; 6,689,880; 6,900,014 and 6,818,807.

SUMMARY OF THE INVENTION

The present invention is related to the transgenic soybean plant designated MON87701 having seed deposited with American Type Culture Collection (ATCC) with Accession No. PTA-8194. Another aspect of the invention is the progeny plants, or seeds, or parts of the plants and seeds of the soybean event MON87701. The plant parts include, but are not limited to pollen, ovule, flowers, shoots, roots, stems, leaves, pods, seeds and meristematic tissues. The soybean plant MON87701 is particularly resistant to insects in the Lepidoptera family such as Velvetbean caterpillar (*Anticarsia gemmatalis*), Soybean looper (*Pseudoplusia includens*), Soybean axil borer (*Epinotia aporema*), Yellow Bear Moth (*Spilosoma virginica*), Corn earworm (*Helicoverpa zea*), Fall armyworm (*Spodoptera frugiperda*) and Sunflower looper (*Rachiplusia nu*) amongst others, all of which are agriculturally important insect pests.

The present invention is also related to the DNA construct of soybean plant MON87701 and the detection of the transgene/genomic insertion region in soybean MON87701 and progeny thereof.

Novel genetic compositions contained in the genome of MON87701 and products from MON87701 such as meal, flour, food products, protein supplements and biomasses remaining in a field from which soybean plants corresponding to MON87701 have been harvested are further aspects of this invention.

According to one aspect of the invention, compositions and methods are provided for detecting the presence of the transgene/genomic insertion region from a novel soybean plant designated MON87701. DNA sequences are provided that comprise at least one junction sequence of MON87701 selected from the group consisting of SEQ ID NO:1 ([A] corresponding to positions 5748 through 5767 of SEQ ID NO:6 [F], FIG. 2) and SEQ ID NO:2 ([B] corresponding to positions 12,174 through 12,193 of SEQ ID NO:6 [F], FIG. 2) and compliments thereof. The junction sequence is a nucleotide sequence that spans the point at which heterologous DNA inserted into the genome is linked to the soybean cell genomic DNA. Detection of this sequence in a biological sample containing soybean DNA is diagnostic for the presence of the soybean event MON87701 DNA in said sample. A soybean event MON87701 and soybean seed comprising these DNA molecules is an aspect of this invention.

DNA sequences that comprise novel transgene/genomic insertion region, SEQ ID NO:3 [C], SEQ ID NO:4 [D] and SEQ ID NO:5 [E] or SEQ ID NO:1 [A], SEQ ID NO:2 [B] and SEQ ID NO:5 [E] (see FIG. 2) from soybean event MON87701 are also aspects of this invention. The soybean plant and seed comprising these molecules are further aspects of this invention.

According to another aspect of the invention, two DNA molecules are provided for use in a DNA detection method. The DNA molecules are of sufficient length of contiguous nucleotides of SEQ ID NO:3 or SEQ ID NO:5 or its complement to function as DNA primers or probes diagnostic for DNA extracted from soybean plant MON87701 or progeny thereof. For Example, the first DNA molecule comprises 11 or more contiguous polynucleotides of any portion of the transgene region of SEQ ID NO:3 or SEQ ID NO:5, or complement thereof, and a second DNA molecule of similar length of any portion of a 5' flanking soybean genomic DNA region of SEQ ID NO:3 or complement thereof, where these DNA molecules when used together are useful as DNA primers in a DNA amplification method that produces an amplicon. The amplicon produced using these DNA primers in the DNA amplification method is diagnostic for soybean event MON87701 when the amplicon contains SEQ ID NO:1. Any amplicon produced by DNA primers homologous or complementary to any portion of SEQ ID NO:3 and SEQ ID NO:5, and any amplicon that comprises SEQ ID NO:1 is an aspect of the invention.

According to another aspect of the invention, two DNA molecules are provided for use in a DNA detection method. The DNA molecules are of sufficient length of contiguous nucleotides of SEQ ID NO:4 or SEQ ID NO:5 or its complement to function as DNA primers or probes diagnostic for DNA extracted from soybean plant MON87701 or progeny thereof. For example, the first DNA molecule comprises 11 or more contiguous polynucleotides of any portion of the transgene region of the DNA molecule of SEQ ID NO:4 or SEQ ID NO:5, or complement thereof, and a second DNA molecule of similar length of any portion of a 3' flanking soybean genomic DNA of SEQ ID NO:4 or complement thereof, where these DNA molecules when used together are useful as DNA primers in a DNA amplification method. The amplicon produced using these DNA primers in the DNA amplification method is diagnostic for soybean event MON87701 when the amplicon contains SEQ ID NO:2. Any amplicons produced by DNA primers homologous or complementary to any portion of SEQ ID NO:4 and SEQ ID NO:5, and any amplicon that comprises SEQ ID NO:2 is an aspect of the invention.

According to another aspect of the invention, two DNA molecules are provided for use in a DNA detection method. The DNA molecules are of sufficient length of contiguous nucleotides of SEQ ID NO:6 or its complement to function as DNA primers or probes diagnostic for DNA extracted from soybean plant MON87701 or progeny thereof. When used together as DNA primers in a DNA amplification method, an amplicon is produced that comprises SEQ ID NO:1 and/or SEQ ID NO:2. The amplicon produced is diagnostic for soybean event MON87701. Any amplicons produced by DNA primers homologous or complementary to any portion of SEQ ID NO:6, and any amplicon that comprises SEQ ID NO:1 and/or SEQ ID NO:2 is an aspect of the invention.

According to another aspect of the invention, methods of detecting the presence of DNA corresponding to the soybean event MON87701 in a biological sample are provided. Such methods comprise: (a) contacting the biological sample with a primer set that, when used in a nucleic acid amplification reaction with genomic DNA from soybean event MON87701, produces an amplicon that is diagnostic for soybean event MON87701; (b) performing a nucleic acid amplification reaction, thereby producing the amplicon; and (c) detecting the amplicon wherein said amplicon comprises SEQ ID NO:1 and/or SEQ ID NO:2, wherein detection of such amplicon is indicative of presence of the DNA corresponding to the soybean event MON87701.

According to another aspect of the invention, methods of detecting the presence of a DNA corresponding to the MON87701 event in a biological sample, such methods comprise: (a) contacting the biological sample with a probe that hybridizes under stringent hybridization conditions with genomic DNA from soybean event MON87701 and does not hybridize under the stringent hybridization conditions with a control soybean plant; (b) subjecting the biological sample and probe to stringent hybridization conditions; and (c) detecting hybridization of the probe to the soybean event MON87701 DNA, wherein detection of such hybridization in indicative of presence of the DNA corresponding to the MON87701 event. Preferably, the probe is selected from the group consisting of SEQ ID NO:1, SEQ ID NO:2 and complement thereof.

A biological sample can comprise any organic material derived from soybean cells or tissue, including stems, roots, leaves, flowers or flower parts, seed or seed pods, and the like, that contains a detectable amount of a nucleotide sequence corresponding to such organic material. A biological sample derived from soybean event MON87701 comprises the transgene/genome insertion regions of the present invention, and particularly those as set forth in the Sequence Listing as shown in SEQ ID NO:1 through SEQ ID NO:6, and the complements thereof.

Kits for the detection of soybean event MON87701 are provided which use primers designed from SEQ ID NO:3, SEQ ID NO:4, SEQ ID NO:5 or SEQ ID NO:6. An amplicon produced using said kit is diagnostic for MON87701 when the amplicon (1) contains either nucleotide sequences set forth as SEQ ID NO:1 or SEQ ID NO:2 or (2) contains both SEQ ID NO:1 and SEQ ID NO:2. The kit can be provided as a means for specifically detecting only the present event MON87701 DNA in a biological sample, or the kit can be provided as a means for detecting a multiplicity of different transgenic events from any number of different biological samples. In the latter case, i.e., a kit for detecting a multiplicity of different transgenic events, the kit may provide probes or primers in the form of a micro array, or any sort of array which provides the user of said kit with the ability to distinguish differences between transgenic and non-transgenic samples, zygosity of transgenic events, and even the presence or absence of events, whether approved or unapproved for commercialization. Detection or scoring of the presence or absence of certain events using such kits can be by fluorometric, colorimetric, isotopic, or luminescent means.

Another aspect of the invention is a soybean plant, or seed, or product derived from the plant or seed of MON87701, in which the genomic DNA when isolated from the soybean plant, or seed, or product comprises a DNA molecule incorporating SEQ ID NO:1 and/or SEQ ID NO:2. Preferably, the genomic DNA thereof comprises a DNA molecule consisting essentially of the nucleotide sequence of SEQ ID NO:3 from about positions 1 to 5757, the nucleotide sequence of SEQ ID NO:5 from about positions 1 to 6426 and the nucleotide sequence of SEQ ID NO:4 from about positions 379 to 2611 (the contig of which is presented as SEQ ID NO:6).

A further aspect of the invention is a soybean plant, or seed, or product derived from the plant or seed of MON87701, wherein the genomic DNA comprises a DNA molecule consisting essentially of the nucleotide sequence of SEQ ID NO:6 from about positions 1 to 14,416.

Another aspect of the invention is a soybean plant, or seed, or product derived from the plant or seed of MON87701, in which the genomic DNA when isolated from the soybean plant, or seed, or product produces an amplicon in a DNA amplification method, wherein said amplicon comprises SEQ ID NO:1 and/or SEQ ID NO:2.

Another aspect of the invention is a method of producing an insect resistant soybean plant. This method comprises: (a) crossing the soybean plant of MON87701 with another soybean plant; (b) obtaining at least one progeny plant derived from the cross of (a); and (c) selecting progeny that comprises nucleotide sequences of SEQ ID NO:1 and SEQ ID NO:2. Said selection includes subjecting the at least one progeny plant obtained from (b) to a nucleic acid amplification reaction, wherein progeny that produces an amplicon comprising at least one nucleotide sequence of SEQ ID NO:3, SEQ ID NO:4, SEQ ID NO:5 or SEQ ID NO:6 is selected, or subjecting the at least one progeny plant obtained from (b) to a nucleic acid hybridization reaction, wherein progeny hybridizing to a probe that hybridizes under stringent conditions with one or more DNA sequence selected from SEQ ID NO:1 and SEQ ID NO:2 is selected. The progeny so-selected is an insect resistant soybean plant.

Another aspect of the invention is a method for protecting a soybean plant from insect infestation. This method comprises providing in the diet of a Lepidopteran pest of soybean an insecticidally effective amount of cell(s) or tissue(s) of the soybean plant MON87701. The Lepidopteran pest is selected from the group consisting of *Anticarsia*, *Pseudoplusia*, *Epinotia*, *Spilosoma*, *Helicoverpa*, *Spodoptera* and *Rachiplusia*.

Another aspect of the invention is commodity product derived from a soybean plant, or seed, or seed progeny of MON87701. Such commodity products include, but are not limited to, whole or processed soy seeds, animal protein feed, vegetable oil, meal, flour, nontoxic plastics, printing inks, lubricants, waxes, hydraulic fluids, electric transformer fluids, solvents, cosmetics, hair care products, soymilk, soy nut butter, natto, tempeh, soy protein concentrate, soy protein isolates, texturized soy protein concentrate, hydrolyzed soy protein, whipped topping, cooking oil, salad oil, shortening, lecithin, edible whole soybeans (raw, roasted, or as edamamé), soymilk, soy yogurt, soy cheese, tofu, yuba and biodiesel.

Another aspect of the invention is a method of determining zygosity of the progeny of soybean event MON87701. The method comprises (a) contacting a soybean sample with the primer pair SQ3443 (SEQ ID NO:12) and SQ3445 (SEQ ID NO:13), that when used in a nucleic acid amplification reaction with genomic DNA from soybean event MON87701, produces an amplicon from the combination of primers SQ3443 and SQ3445 that is diagnostic for soybean event MON87701; (b) performing a nucleic acid amplification reaction; (c) detecting a first amplicon produced; (d) contacting the same sample with the primer pair SQ3445 (SEQ ID NO:13) and SQ3446 (SEQ ID NO:14), that when used in a nucleic acid amplification reaction with genomic DNA from soybean plants produces an amplicon from the combination of primers SQ3445 and SQ3446 that is diagnostic of the wild-type soybean genomic DNA homologous to the soybean genomic region of a transgene insertion identified as soybean event MON87701; (e) performing a nucleic acid amplification reaction, and (f) detecting a second amplicon produced; wherein detection of both amplicons indicates that the soybean sample is heterozygous for soybean event MON87701 DNA.

Another aspect of the invention is a method of determining zygosity of the progeny of soybean event MON87701 further using probes labeled with fluorophore(s). Such method comprises (a) contacting a soybean sample with the primer pair SQ3443 (SEQ ID NO:12), SQ3445 (SEQ ID NO:13), and the probe 6FAM™-labeled PB1111 (SEQ ID NO:15), that when used in a nucleic acid amplification reaction with genomic DNA from soybean event MON87701, produces an amplicon that is diagnostic for soybean event MON87701, releasing a fluorescent signal from the combination of primers SQ3443 and SQ3445 and probe 6FAM™-labeled PB1111; (b) performing a nucleic acid amplification reaction; (c) detecting a first amplicon produced; (d) contacting the same sample with the primer pair SQ3445 (SEQ ID NO:13) and SQ3446 (SEQ ID NO:14) and a VIC™-labeled PB1112 (SEQ ID NO:16), that when used in a nucleic acid amplification reaction with genomic DNA from soybean plants, produces an amplicon that is diagnostic for wild-type soybean genomic DNA homologous to the soybean genomic region of a transgene insertion identified as soybean event MON87701, releasing a fluorescent signal from the combination of primers SQ3445 and SQ3446 and probe VIC™-labeled PB 1112; (e) performing a nucleic acid amplification reaction; and (f) detecting a second amplicon produced; wherein detection of both amplicons indicates that the soybean sample comprising DNA that is heterozygous for the transgene insertion identified as soybean event MON87701.

The foregoing and other aspects of the invention will become more apparent from the following detailed description.

BRIEF DESCRIPTION OF THE SEQUENCES

Figure 2:
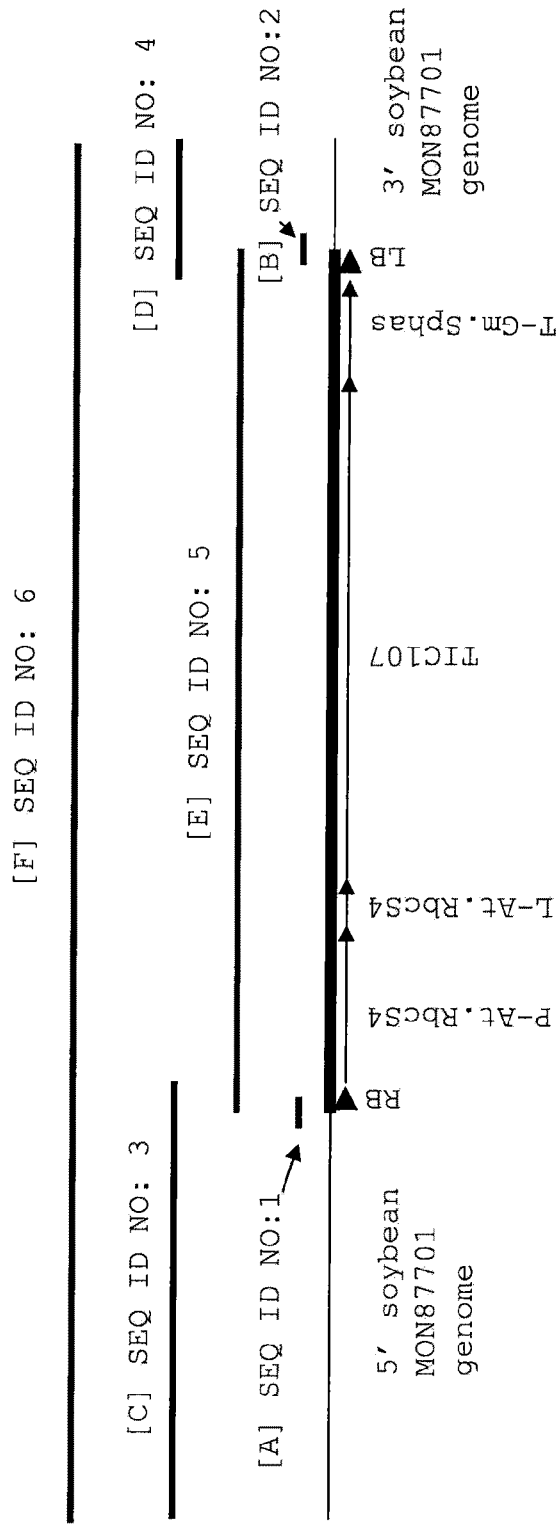
FIG. 2 illustrates organization of the transgenic insert in the genome of soybean event MON87701: [A] corresponds to the relative position of SEQ ID NO:1 which forms the junction between SEQ ID NO:3 and SEQ ID NO:5; [B] corresponds to the relative position of SEQ ID NO:2 which forms the junction between SEQ ID NO:4 and SEQ ID NO:5; [C] corresponds to the relative position of SEQ ID NO:3, the soybean genome sequence flanking the arbitrarily assigned/designated 5' end of the expression cassette integrated into the genome in event MON87701; [D] corresponds to the relative position of SEQ ID NO:4, the soybean genome sequence flanking the arbitrarily assigned/designated 3' end of the expression cassette integrated into the genome in event MON87701; [E] represents the various elements comprising SEQ ID NO:5 and is the sequence of the expression cassette inserted into the genome of the event MON87701; and [F] represents the contiguous sequence comprising, as represented in the figure from left to right, SEQ ID NO:3, SEQ ID NO:5 and SEQ ID NO:4, in which SEQ ID NO:1 and SEQ ID NO:2 are incorporated as set forth above, as these sequences are present in the genome in event MON87701.

SEQ ID NO:1—A 20 nucleotide sequence representing the junction between the soybean genomic DNA and the integrated expression cassette (see FIG. 2). This sequence corresponds to positions 5748 to 5767 of SEQ ID NO:6. In addition, SEQ ID NO: 1 ([A]) is a nucleotide sequence corresponding to positions 5748 through 5757 of SEQ ID NO:3 ([C]) and the integrated right border of the TIC107 expression cassette corresponding to positions 1 through 10 of SEQ ID NO:5 ([E]). SEQ ID NO:1 also corresponds to positions 5748 to 5767 of the 5' flanking sequence, SEQ ID NO:3 ([C]).

SEQ ID NO:2—A 20 nucleotide sequence representing the junction between the integrated expression cassette and the soybean genomic DNA (see FIG. 2). This sequence corresponds to positions 12174 to 12193 of SEQ ID NO:6 ([F]). In addition, SEQ ID NO:2 ([B]) is a nucleotide sequence corresponding positions 6417 through 6426 of SEQ ID NO:5 ([E]) and the 3' flanking sequence corresponding to positions 379 through 388 of SEQ ID NO:4 ([D]). SEQ ID NO:2 ([B]) also corresponds to positions 369 to 388 of the 3' flanking sequence, SEQ ID NO:4 ([D]).

SEQ ID NO:3 ([C] of FIG. 2)—The 5' sequence flanking the inserted DNA of MON87701 up to and including a region of transformation DNA (T-DNA) insertion.

SEQ ID NO:4 ([D] of FIG. 2)—The 3' sequence flanking the inserted DNA of MON87701 up to and including a region of T-DNA insertion.

SEQ ID NO:5 ([E] of FIG. 2)—The sequence of the integrated TIC107 expression cassette, including right and left border sequence after integration.

SEQ ID NO:6 ([F] of FIG. 2)—A 14,416 bp nucleotide sequence representing the contig of the 5' sequence flanking the inserted DNA of MON87701 (SEQ ID NO:3), the sequence of the integrated expression cassette (SEQ ID NO:5) and the 3' sequence flanking the inserted DNA of MON87701 (SEQ ID NO:4).

SEQ ID NO:7—The TIC107 expression cassette of pMON53570.

SEQ ID NO:8—The sequence of the TIC107 encoding DNA, including nucleotides encoding the chloroplast transit peptide.

SEQ ID NO:9—Primer SQ1135 used to identify MON87701 events. Primer SQ1135 is complimentary to the 5' region of the inserted expression cassette, close to the right T-DNA insertion border corresponding to positions 5790 to 5766 of SEQ ID NO:6 and positions 33 to 9 of SEQ ID NO:5.

SEQ ID NO:10—Primer SQ1136 used to identify MON87701 events. Primer SQ1136 corresponds to a 5' region flanking the inserted expression cassette close to the right T-DNA insertion border corresponding to positions 5705 to 5732 of SEQ ID NO:6 and positions 5705 to 5732 of SEQ ID NO:3. A PCR amplicon of about 86 bp produced using the combination of primers SQ1135 and SQ1136 is positive for the presence of the event MON87701.

SEQ ID NO:11—Probe PB63 used to identify MON87701 events. This probe is a 6FAM™-labeled synthetic oligonucleotide whose sequence is complimentary to positions 5763 to 5748 of SEQ ID NO:6. Release of a fluorescent signal in an amplification reaction using primers SQ1135 and SQ1136 in combination with 6FAM™-labeled probe PB63 is diagnostic of event MON87701.

SEQ ID NO:12—Primer SQ3443 used to determine zygosity of MON87701 events. Primer SQ3443 corresponds to a region of the inserted expression cassette, close to the left T-DNA border, corresponding to positions 12145 to 12168 of SEQ ID NO:6 and to positions 6388 to 6411 of SEQ ID NO:5.

SEQ ID NO:13—Primer SQ3445 used to determine zygosity of MON87701 events. Primer SQ3445 is complimentary to the 3' region flanking the inserted expression cassette, close to the left T-DNA corresponding to positions 12215 to 12188 of SEQ ID NO:6 and to positions 410 to 383 SEQ ID NO:4. Detection of a PCR amplicon using primers SQ3443 and SQ3445 with or without 6FAM™-labeled Probe PB1111 is positive for presence of event MON87701 in a zygosity assay.

SEQ ID NO:14—Primer SQ3446 used to determine zygosity of MON87701 events. Primer SQ3446 corresponds to a region of the wild-type genomic DNA wherein insertion of the expression cassette for MON87701 occurred. Detection of a PCR amplicon using primer SQ3445 and SQ3446 with or without VIC™-labeled probe PB1112 is positive for the presence of the wild-type allele.

SEQ ID NO:15—Probe PB 1111 used to determine zygosity of MON87701 events. This probe is a 6FAM™-labeled synthetic oligonucleotide whose sequence corresponds to positions 12172 to 12187 of SEQ ID NO:6. A PCR amplicon produced using primers SQ3443 and SQ3445 causes the release of a fluorescent signal using probe PB1111, which is positive for the presence of event MON87701 in a zygosity assay for MON87701 event.

SEQ ID NO:16—Probe PB1112 used to determine zygosity of MON87701 events. This probe is a VIC™-labeled synthetic oligonucleotide whose sequence corresponds to a region of the wild-type genomic DNA immediately following the region of homology to primer SQ3446 at the point of insertion of the expression cassette for event MON87701. A PCR amplicon produced using primers SQ3445 and SQ3446 causes the release of a fluorescent signal using probe PB1112, which is positive for the presence of the wild-type allele in a zygosity assay for MON87701 event. Heterozygosity of the MON87701 event is demonstrated by the fluorescent detection of two different amplicons using probes PB1111 and PB1112 in an amplification reaction using primers SQ3443, SQ3445 and SQ3446.

DETAILED DESCRIPTION OF THE PREFERRED EMBODIMENTS

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994.

As used herein, the term "soybean" means *Glycine max* and includes all plant varieties that can be bred with soybean, including wild soybean species as well as those plants belonging to *Glycine soja* that permit breeding between species.

As used herein, the term "comprising" means "including but not limited to".

The term "glyphosate" refers to N-phosphonomethylglycine and its salts. N-phosphonomethylglycine is a well-known herbicide that has activity on a broad spectrum of plant species.

A "commodity product" refers to any product which is comprised of material derived from soybean or soybean oil and is sold to consumers. Processed soybeans are the largest source of protein feed and vegetable oil in the world. The soybean plant MON87701 can be used to manufacture commodities typically acquired from soy. Soybeans of MON87701 can be processed into meal, flour, as well as be used as a protein source in animal feeds for both terrestrial and aquatic animals. Soybeans and soybean oils from MON87701 can be used in the manufacture of many different products, not limited to, nontoxic plastics, printing inks, lubricants, waxes, hydraulic fluids, electric transformer fluids, solvents, cosmetics, and hair care products. Soybeans and soybean oils of MON87701 are suitable for use in a variety of soyfoods made from whole soybeans, such as soymilk, soy nut butter, natto, and tempeh, and soyfoods made from processed soybeans and soybean oil, including soybean meal, soy flour, soy protein concentrate, soy protein isolates, texturized soy protein concentrate, hydrolyzed soy protein, whipped topping, cooking oil, salad oil, shortening, and lecithin. Whole soybeans are also edible, and are typically sold to consumers raw, roasted, or as edamamé. Soymilk, which is typically produced by soaking and grinding whole soybeans, may be consumed without other processing, spray-dried, or processed to form soy yogurt, soy cheese, tofu, or yuba.

Soybean Oils of MON87701 can be used to make biodiesel. The use of biodiesel in conventional diesel engines results in substantial reductions of pollutants such as sulfates, carbon monoxide, and particulates compared to petroleum diesel fuel, and use in school buses can greatly reduce exposure to toxic diesel exhaust. Biodiesel is typically obtained by extracting, filtering and refining soybean oil to remove free fats and phospholipids, and then transesterifying the oil with methanol to form methyl esters of the fatty acids (see for example U.S. Pat. No. 5,891,203). The resultant soy methyl esters are commonly referred to as "biodiesel." The oil derived from MON87701 may also be used as a diesel fuel without the formation of methyl esters, such as, for example, by mixing acetals with the oil (see for example U.S. Pat. No. 6,013,114). The seeds of MON87701 used to make said oils can be identified by the methods of the present invention. It is expected that purified oil from MON87701 event seeds or mixtures of seeds some or all of which are MON87701 will have relatively no DNA available for testing. However, the seeds from which the oils are extracted can be characterized with the method of the present invention to identify the presence of the MON87701 event within the population of seeds used to make said oils. Also, plant waste from the process used to make said oils can be used in the methods of the present invention to identify the presence of MON87701 events within a mixture of seeds processed to make said oils. Likewise, plant debris left after making a commodity product, or left behind following harvest of the soybean seed, can be characterized by the methods of the present invention to identify MON87701 events within the raw materials used to make said commodity products.

A transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that include the heterologous DNA. Even after repeated backcrossing to a recurrent parent, the inserted DNA and flanking DNA from the transformed parent is present in the progeny of the cross at the same chromosomal location. The term "event" also refers to DNA from the original transformant comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selling) and a parental line that does not contain the inserted DNA. The present invention relates to the event MON87701 DNA, plant cells, tissues, seeds and processed products derived from MON87701.

It is also to be understood that two different transgenic plants can also be mated to produce offspring that contain two independently segregating added, exogenous genes. Selfing of appropriate progeny can produce plants that are homozygous for both added, exogenous genes. Back-crossing to a parental plant and out-crossing with a non-transgenic plant are also contemplated, as is vegetative propagation. Descriptions of other breeding methods that are commonly used for different traits and crops can be found in one of several references, e.g., Fehr, in *Breeding Methods for Cultivar Development*, Wilcox J. ed., American Society of Agronomy, Madison Wis. (1987).

As used herein when referring to an "isolated DNA molecule", it is intended that the DNA molecule be one that is present, alone or in combination with other compositions, but not within its natural environment. For example, a coding sequence, intron sequence, untranslated leader sequence, promoter sequence, transcriptional termination sequence, and the like, that are naturally found within the DNA of a soybean genome are not considered to be isolated from the soybean genome so long as they are within the soybean genome. However, each of these components, and subparts of these components, would be "isolated" within the scope of this disclosure so long as the structures and components are not within the soybean genome. Similarly, a nucleotide sequence encoding a *Bacillus thuringiensis* insecticidal protein or any insecticidal variant of that protein would be an isolated nucleotide sequence so long as the nucleotide sequence was not within the DNA of the *Bacillus thuringiensis* bacterium from which the structure was first observed. An artificial nucleotide sequence encoding the same amino acid sequence or a substantially identical amino acid sequence that the native *B. thuringiensis* nucleotide sequence encodes would be considered to be isolated for the purposes of this disclosure. For the purposes of this disclosure, any transgenic nucleotide sequence, i.e., the nucleotide sequence of the DNA inserted into the genome of the cells of the soybean plant event MON87701 would be considered to be an isolated nucleotide sequence whether it is present within the plasmid used to transform soybean cells from which the MON87701 event arose, within the genome of the event MON87701, present in detectable amounts in tissues, progeny, biological samples or commodity products derived from the event MON87701. The nucleotide sequence or any fragment derived therefrom would therefore be considered to be isolated or isolatable if the DNA molecule can be extracted from cells, or tissues, or homogenate from a plant or seed or plant organ; or can be produced as an amplicon from extracted DNA or RNA from cells, or tissues, or homogenate from a plant or seed or plant organ, any of which is derived from such materials derived from the event MON87701. For that matter, the junction sequences as set forth at SEQ ID NO:1 and SEQ ID NO:2, and nucleotide sequences derived from event MON87701 that also contain these junction sequences are considered to be isolated or isolatable, whether these sequences are present within the genome of the cells of event MON87701 or present in detectable amounts in tissues, progeny, biological samples or commodity products derived from the event MON87701.

A "probe" is an isolated nucleic acid to which is attached a conventional detectable label or reporter molecule, e.g., a radioactive isotope, ligand, chemilluminescent agent, or enzyme. Such a probe is complementary to a strand of a target nucleic acid, in the case of the present invention, to a strand of genomic DNA from soybean event MON87701 whether from a soybean plant or from a sample that includes DNA from the event. Probes according to the present invention include not only deoxyribonucleic or ribonucleic acids but also polyamides and other probe materials that bind specifically to a target DNA sequence and such binding can be used to detect the presence of that target DNA sequence.

"Primers" are isolated nucleic acids that are annealed to a complementary target DNA strand by nucleic acid hybridization to form a hybrid between the primer and the target DNA strand, and then extended along the target DNA strand by a polymerase, e.g., a DNA polymerase. Primer pairs of the present invention refer to their use for amplification of a target nucleic acid sequence, e.g., by the polymerase chain reaction (PCR) or other conventional nucleic acid amplification methods.

Probes and primers are generally 11 nucleotides or more in length, preferably 18 nucleotides or more, more preferably 24 nucleotides or more, and most preferably 30 nucleotides or more. Such probes and primers hybridize specifically to a target sequence under high stringency hybridization conditions. Preferably, probes and primers according to the present invention have complete sequence similarity with the target sequence, although probes differing from the target sequence and that retain the ability to hybridize to target sequences may be designed by conventional methods.

Methods for preparing and using probes and primers are described, for example, in *Molecular Cloning: A Laboratory Manual,* 2nd ed., vol. 1-3, ed. Sambrook et al., Cold Spring Harbor Laboratory Press, Cold Spring Harbor, N.Y., 1989 (hereinafter, "Sambrook et al., 1989"); *Current Protocols in Molecular Biology*, ed. Ausubel et al., Greene Publishing and Wiley-Interscience, New York, 1992 (with periodic updates) (hereinafter, "Ausubel et al., 1992"); and Innis et al., *PCR Protocols: A Guide to Methods and Applications*, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Primers and probes based on the flanking DNA and insert sequences disclosed herein can be used to confirm (and, if necessary, to correct) the disclosed sequences by conventional methods, e.g., by re-cloning and sequencing such sequences.

The nucleic acid probes and primers of the present invention hybridize under stringent conditions to a target DNA sequence. Any conventional nucleic acid hybridization or amplification method can be used to identify the presence of DNA from a transgenic event in a sample. Nucleic acid molecules or fragments thereof are capable of specifically hybridizing to other nucleic acid molecules under certain circumstances. As used herein, two nucleic acid molecules are said to be capable of specifically hybridizing to one another if the two molecules are capable of forming an anti-parallel, double-stranded nucleic acid structure. A nucleic acid molecule is said to be the "complement" of another nucleic acid molecule if they exhibit complete complementarity. As used herein, molecules are said to exhibit "complete complementarity" when every nucleotide of one of the molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions. Conventional stringency conditions are described by Sambrook et al., 1989, and by Haymes et al., In: *Nucleic Acid Hybridization, A Practical Approach*, IRL Press, Washington, D.C. (1985), Departures from complete complementarity are therefore permissible, as long as such departures do not completely preclude the capacity of the molecules to form a double-stranded structure. In order for a nucleic acid molecule to serve as a primer or probe it need only be sufficiently complementary in sequence to be able to form a stable double-stranded structure under the particular solvent and salt concentrations employed.

As used herein, a "substantially homologous sequence" is a nucleic acid sequence that will specifically hybridize to the complement of the nucleic acid sequence to which it is being compared under high stringency conditions. Appropriate stringency conditions which promote DNA hybridization, for example, 6.0× sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed. In a preferred embodiment, a nucleic acid of the present invention will specifically hybridize to one or more of the nucleic acid molecules set forth in SEQ ID NO:1 and 2 or complements thereof or fragments of either under moderately stringent conditions, for example at about 2.0×SSC and about 65° C. In a particularly preferred embodiment, a nucleic acid of the present invention will specifically hybridize to one or more of the nucleic acid molecules set forth in SEQ ID NO:1 and SEQ ID NO:2 or complements or fragments of either under high stringency conditions. In one aspect of the present invention, a preferred marker nucleic acid molecule of the present invention has the nucleic acid sequence set forth in SEQ ID NO:1 and SEQ ID NO:2 or complements thereof or fragments of either. In another aspect of the present invention, a preferred marker nucleic acid molecule of the present invention shares 80%, 81%, 82%, 83%, 84%, 85%, 86%, 87%, 88%, 89%, 90%, 91%, 92%, 93%, 94%, 95%, 96%, 97%, 98%, 99% and 100% sequence identity with the nucleic acid sequence set forth in SEQ ID NO:1 and SEQ ID NO:2 or complement thereof or fragments of either. In a further aspect of the present invention, a preferred marker nucleic acid molecule of the present invention shares 95% 96%, 97%, 98%, 99% and 100% sequence identity with the sequence set forth in SEQ ID NO:1 and SEQ ID NO:2 or complement thereof or fragments of either. SEQ ID NO:1 and SEQ ID NO:2 may be used as markers in plant breeding methods to identify the progeny of genetic crosses similar to the methods described for simple sequence repeat DNA marker analysis, in "DNA markers: Protocols, applications, and overviews: (1997) 173-185, Cregan, et al., eds., Wiley-Liss NY"; all of which is herein incorporated by reference. The hybridization of the probe to the target DNA molecule can be detected by any number of methods known to those skilled in the art, these can include, but are not limited to, fluorescent tags, radioactive tags, antibody based tags, and chemilluminescent tags.

Regarding the amplification of a target nucleic acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product, the amplicon, in a DNA thermal amplification reaction.

The term "specific for (a target sequence)" indicates that a probe or primer hybridizes under stringent hybridization conditions only to the target sequence in a sample comprising the target sequence.

As used herein, "amplified DNA" or "amplicon" refers to the product of nucleic acid amplification of a target nucleic acid sequence that is part of a nucleic acid template. For example, to determine whether the soybean plant resulting from a sexual cross contains transgenic event genomic DNA from the soybean plant of the present invention, DNA extracted from a soybean plant tissue sample may be subjected to nucleic acid amplification method using a primer pair that includes a primer derived from flanking sequence in the genome of the plant adjacent to the insertion site of inserted heterologous DNA, and a second primer derived from the inserted heterologous DNA to produce an amplicon that is diagnostic for the presence of the event DNA. The amplicon is of a length and has a sequence that is also diagnostic for the event. The amplicon may range in length from the combined length of the primer pairs plus one nucleotide base pair, preferably plus about fifty nucleotide base pairs, more preferably plus about two hundred-fifty nucleotide base pairs, and even more preferably plus about four hundred-fifty nucleotide base pairs. Alternatively, a primer pair can be derived from flanking sequence on both sides of the inserted DNA so as to produce an amplicon that includes the entire insert nucleotide sequence. A member of a primer pair derived from the plant genomic sequence may be located a distance from the inserted DNA molecule, this distance can range from one nucleotide base pair up to about twenty thousand nucleotide base pairs. The use of the term "amplicon" specifically excludes primer dimers that may be formed in the DNA thermal amplification reaction.

Nucleic acid amplification can be accomplished by any of the various nucleic acid amplification methods known in the art, including the polymerase chain reaction (PCR). A variety of amplification methods are known in the art and are described, inter alia, in U.S. Pat. Nos. 4,683,195 and 4,683,202 and in *PCR Protocols: A Guide to Methods and Applications*, ed. Innis et al., Academic Press, San Diego, 1990. PCR amplification methods have been developed to amplify up to 22 kb of genomic DNA and up to 42 kb of bacteriophage DNA (Cheng et al., Proc. Natl. Acad. Sci. USA 91:5695-5699, 1994). These methods as well as other methods known in the art of DNA amplification may be used in the practice of the present invention. The sequence of the heterologous DNA insert or flanking sequence from soybean event MON87701 with seed samples deposited as ATCC PTA-8194 can be verified (and corrected if necessary) by amplifying such sequences from the event using primers derived from the sequences provided herein followed by standard DNA sequencing of the PCR amplicon or of the cloned DNA.

The amplicon produced by these methods may be detected by a plurality of techniques. One such method is Genetic Bit Analysis (Nikiforov, et al. Nucleic Acid Res. 22:4167-4175, 1994) where a DNA oligonucleotide is designed which overlaps both the adjacent flanking genomic DNA sequence and the inserted DNA sequence. The oligonucleotide is immobilized in wells of a microwell plate. Following PCR of the region of interest (using one primer in the inserted sequence and one in the adjacent flanking genomic sequence), a single-stranded PCR product can be hybridized to the immobilized oligonucleotide and serve as a template for a single base extension reaction using a DNA polymerase and labelled ddNTPs specific for the expected next base. Readout may be fluorescent or ELISA-based. A signal indicates presence of the insert/flanking sequence due to successful amplification, hybridization, and single base extension.

Another method is the Pyrosequencing technique as described by Winge (Innov. Pharma. Tech. 00:18-24, 2000). In this method an oligonucleotide is designed that overlaps the adjacent genomic DNA and insert DNA junction. The oligonucleotide is hybridized to single-stranded PCR product from the region of interest (one primer in the inserted sequence and one in the flanking genomic sequence) and incubated in the presence of a DNA polymerase, ATP, sulfurylase, luciferase, apyrase, adenosine 5' phosphosulfate and luciferin. dNTPs are added individually and the incorporation results in a light signal which is measured. A light signal indicates the presence of the transgene insert/flanking sequence due to successful amplification, hybridization, and single or multi-base extension.

Fluorescence Polarization as described by Chen, et al., (Genome Res. 9:492-498, 1999) is a method that can be used to detect the amplicon of the present invention. Using this method an oligonucleotide is designed which overlaps the genomic flanking and inserted DNA junction. The oligonucleotide is hybridized to single-stranded PCR product from the region of interest (one primer in the inserted DNA and one in the flanking genomic DNA sequence) and incubated in the presence of a DNA polymerase and a fluorescent-labeled ddNTP. Single base extension results in incorporation of the ddNTP. Incorporation can be measured as a change in polarization using a fluorometer. A change in polarization indicates the presence of the transgene insert/flanking sequence due to successful amplification, hybridization, and single base extension.

TAQMAN® (PE Applied Biosystems, Foster City, Calif.) is described as a method of detecting and quantifying the presence of a DNA sequence and is fully understood in the instructions provided by the manufacturer. Briefly, a FRET oligonucleotide probe is designed which overlaps the genomic flanking and insert DNA junction. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization.

Molecular Beacons have been described for use in sequence detection as described in Tyangi, et al. (Nature Biotech. 14:303-308, 1996). Briefly, a FRET oligonucleotide probe is designed that overlaps the flanking genomic and insert DNA junction. The unique structure of the FRET probe results in it containing secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe to the target sequence results in the removal of the probe secondary structure and spatial separation of the fluorescent and quenching moieties that in turn results in the production of a fluorescent signal. The fluorescent signal indicates the presence of the flanking/transgene insert sequence due to successful amplification and hybridization.

Other described methods, such as, microfluidics (US Patent pub. 2006068398, U.S. Pat. No. 6,544,734) provide methods and devices to separate and amplify DNA samples. Optical dyes used to detect and quantitate specific DNA molecules (WO/05017181). Nanotube devices (WO/06024023) that comprise an electronic sensor for the detection of DNA molecules or nanobeads that bind specific DNA molecules and can then be detected.

DNA detection kits can be developed using the compositions disclosed herein and the methods well known in the art of DNA detection. The kits are useful for the identification of soybean event MON87701 DNA in a sample and can be applied to methods for breeding soybean plants containing the appropriate event DNA. The kits may contain DNA primers or probes that are homologous or complementary to SEQ ID NO:1 through SEQ ID NO:6 or DNA primers or probes homologous or complementary to DNA sequence of the genetic elements contained in the transgene insert. These DNA sequences can be used as primers in DNA amplification reactions or as probes in a DNA hybridization method. The sequences of the genomic DNA and transgene genetic elements contained in MON87701 soybean genome as illustrated in FIG. 2, consists of a portion of the right border region (RB) from *Agrobacterium tumefaciens*, a promoter sequence derived from the *Arabidopsis* ribulose 1,5-bisphosphate carboxylase small subunit gene (herein referred to as P-RbcS4 located at positions 155 to 1850 on SEQ ID NO:5) is operably linked to an untranslated leader sequence derived from the *Arabidopsis* ribulose 1,5-bisphosphate carboxylase small subunit gene (herein referred to as L-RbcS4 located at positions 1851 to 1877 on SEQ ID NO:5) operably connected to the insect toxin coding sequence, TIC107, which is comprised of a chloroplast transit peptide derived from transit peptide sequence of the *Arabidopsis* ribulose 1,5-bisphosphate carboxylase small subunit gene and an insect toxin derived from Cry1Ac (herein referred to as TIC107 located at positions 1889 to 2141 for the transit peptide and positions 2142 to 5678 for the toxin coding sequence, respectively on SEQ ID NO:5) and is operably connected to a 3' termination region derived from the *Glycine max* 7S alpha' beta conglycinin storage protein gene (herein referred to as T-Sphas located at positions 5688 to 6126 on SEQ ID NO:5) and a portion of the left border (LB) region from *Agrobacterium tumefaciens*. DNA molecules useful as primers in DNA amplification methods can be derived from the sequences of the genetic elements of the transgene insert contained in the MON87701 event. These primer molecules can be used as part of a primer set that also includes a DNA primer molecule derived from the genome flanking the transgene insert of event MON87701 as presented in SEQ ID NO:3 from bases 1 through 5747 and SEQ ID NO:4 from bases 389 through 2611.

Figure 1:
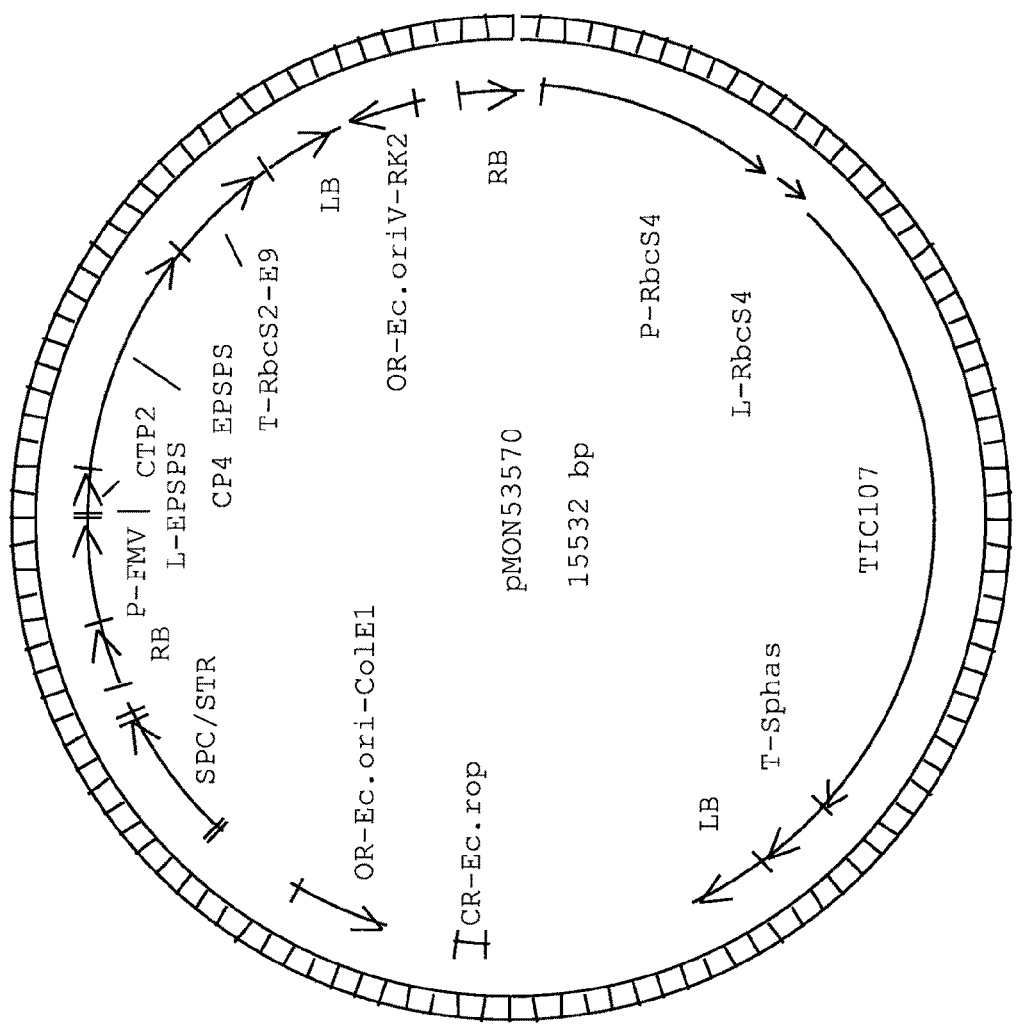
FIG. 1 illustrates the map of binary transformation vector, pMON53570 that was used to generate soybean plant MON87701.

The soybean plant MON87701 was produced by an *Agrobacterium* mediated transformation process of an inbred soybean line with the plasmid construct pMON53570 (as shown in FIG. 1). The transformation method used is similar to that described in U.S. Pat. No. 5,914,451. The plasmid construct pMON53570 contains the linked plant expression cassettes with the regulatory genetic elements necessary for expression of the TIC107 protein in soybean plant cells. Soybean cells were regenerated into intact soybean plants and individual plants were selected from the population of plants that showed integrity of the plant expression cassettes and resistance to Lepidopteran insect larvae feeding damage as well as a loss of the unlinked glyphosate resistance selection cassette. A soybean plant that contains in its genome the linked plant expression cassettes of pMON53570 is an aspect of the present invention.

The plasmid DNA inserted into the genome of soybean plant MON87701 was characterized by detailed molecular analyses. These analyses included: the insert number (number of integration sites within the soybean genome), the copy number (the number of copies of the T-DNA within one locus), and the integrity of the inserted gene cassettes. DNA molecular probes were used that included the intact TIC107 coding region and its respective regulatory elements, the promoters, introns, and polyadenylation sequences of the plant expression cassettes, and the plasmid pMON53570 backbone DNA region. The data show that MON87701 contains a single T-DNA insertion with one copy of the TIC107 expression cassette. No additional elements from the transformation vector pMON53570, linked or unlinked to intact gene cassettes, were detected in the genome of MON87701. Finally, Inverse PCR and DNA sequence analyses were performed to determine the 5' and 3' insert-to-plant genome junctions, confirm the organization of the elements within the insert (FIG. 2), and determine the complete DNA sequence of the insert in soybean plant MON87701 (SEQ ID NO:5).

The present invention is directed to a DNA molecule comprising a nucleotide sequence of SEQ ID NO:1, SEQ ID NO:2, or complement thereof. The DNA molecule preferably comprises a nucleotide sequence of SEQ ID NO:3, SEQ ID NO:4, SEQ ID NO:5, SEQ ID NO:6 or complement thereof. Still preferably, the DNA molecule consists essentially of the nucleotide sequence of SEQ ID NO:3 from positions 1 to 5757, the nucleotide sequence of SEQ ID NO:5 from positions 1 to 6426, and the nucleotide sequence of SEQ ID NO:4 from positions 379 to 2611, or complement thereof, or essentially of the nucleotide sequence of SEQ ID NO:6 or complement thereof.

The present invention is also directed to a soybean plant, or parts thereof, or seed that comprises the DNA molecule.

A composition derived from the soybean plant, or parts thereof, of the present invention is also provided. Such composition comprises a detectable amount of the DNA molecule and is a commodity product selected from soybean meal, soy flour, soy protein concentrate, soy protein isolates, texturized soy protein concentrate, hydrolyzed soy protein, soybean oil and whipped topping.

The present invention is further directed to a method of producing an insect resistant soybean plant. This method comprises: (a) crossing the soybean plant of MON87701 with another soybean plant; (b) obtaining at least one progeny plant derived from the cross of (a); and (c) selecting progeny that comprises nucleotide sequences of SEQ ID NO:1 and SEQ ID NO:2. Said selection includes subjecting the at least one progeny plant obtained from (b) to a nucleic acid amplification reaction, wherein progeny that produces an amplicon comprising at least one nucleotide sequence of SEQ ID NO:3, SEQ ID NO:4, SEQ ID NO:5 or SEQ ID NO:6 is selected, or subjecting the at least one progeny plant obtained from (b) to a nucleic acid hybridization reaction, wherein progeny hybridizing to a probe that hybridizes under stringent conditions with one or more DNA sequence selected from SEQ ID NO:1 and SEQ ID NO:2 is selected. The progeny so-selected is an insect resistant soybean plant.

The present invention is still further directed to a method for protecting a soybean plant from insect infestation. This method comprises providing in the diet of a Lepidopteran pest of soybean an insecticidally effective amount of cell(s) or tissue(s) of the soybean plant MON87701. The Lepidopteran pest is selected from the group consisting of *Anticarsia*, *Pseudoplusia*, *Epinotia*, *Spilosoma*, *Helicoverpa*, *Spodoptera* and *Rachiplusia*.

Still further provided in the present invention is a pair of DNA molecules comprising a first DNA molecule and a second DNA molecule, wherein the DNA molecules are of sufficient length of contiguous nucleotides of SEQ ID NO:3 or SEQ ID NO:5 or its complement; or SEQ ID NO:4 or SEQ ID NO:5 or its complement; or SEQ ID NO:6 or its complement; to function as DNA primers or probes diagnostic for DNA extracted from soybean plant MON87701 or progeny thereof.

For example, the first DNA molecule of the pair comprises 11 or more contiguous nucleotides of any portion of the transgene region of SEQ ID NO:3 or SEQ ID NO:5, or complement thereof, and the second DNA molecule of the pair comprises a similar length of a 5' flanking soybean genomic DNA region of SEQ ID NO:3, or complement thereof. A specific example is that the first DNA molecule comprises SEQ ID NO:9 and the second DNA molecule comprises SEQ ID NO:10.

Another example is that the first DNA molecule of the pair comprises 11 or more contiguous nucleotides of any portion of the transgene region of SEQ ID NO:4 or SEQ ID NO:5, or complement thereof, and the second DNA molecule of the pair comprises a similar length of a 3' flanking soybean genomic DNA region of SEQ ID NO:4, or complement thereof. A specific example is that the first DNA molecule comprises SEQ ID NO:12 and the second DNA molecule comprises SEQ ID NO:13.

The present invention is further directed to a method of detecting the presence of a DNA molecule selected from the group consisting of SEQ ID NO:3, SEQ ID NO:4, SEQ ID NO:5 and SEQ ID NO:6 in a biological sample. This method comprises: (a) contacting the biological sample with a DNA primer pair comprising DNA primer molecules of sufficient length of contiguous nucleotides of SEQ ID NO:3 or its complement, SEQ ID NO:4 or its complement, SEQ ID NO:5 or its complement, or SEQ ID NO:6 or its complement, to function as DNA primers or probes diagnostic for DNA extracted from soybean plant MON87701 or progeny thereof; (b) providing a nucleic acid amplification reaction condition; (c) performing the nucleic acid amplification reaction, thereby producing a DNA amplicon molecule; and (d) detecting the DNA amplicon molecule so produced. Detection of an amplicon comprising at least one of SEQ ID NO:1, SEQ ID NO:2 and complement thereof is indicative of the presence of the DNA molecule in the biological sample.

The biological sample can comprise any organic material derived from soybean cells or tissue, including stems, roots, leaves, flowers or flower parts, seed or seed pods, and the like, that contains a detectable amount of a nucleotide sequence corresponding to such organic material. A biological sample derived from soybean event MON87701 comprises the transgene/genome insertion regions of the present invention, and particularly those as set forth in the Sequence Listing as shown in SEQ ID NO:1 through SEQ ID NO:6, and the complements thereof. For example, the biological sample suitable for the present invention can be soybean meal, soy flour, soy protein concentrate, soy protein isolates, texturized soy protein concentrate, hydrolyzed soy protein and whipped topping. The sample being tested can be a DNA sample extracted from a soybean plant.

The present invention is still further directed to a method of detecting the presence of a DNA molecule selected from the group consisting of SEQ ID NO:3, SEQ ID NO:4, SEQ ID NO:5 and SEQ ID NO:6 in a biological sample. Such method comprises: (a) contacting the biological sample with a DNA probe that hybridizes under stringent conditions with said DNA molecule, and does not hybridize under the stringent conditions with a biological sample not containing the DNA molecule; (b) subjecting the biological sample and DNA probe to stringent hybridization conditions; and (c) detecting hybridization of the DNA probe to the biological sample. Detection of hybridization is indicative of the presence of the DNA molecule in the biological sample. For example, the biological sample being tested can be a DNA sample extracted from a soybean plant.

The probes used in the above detection method can comprise SEQ ID NO:1 or SEQ ID NO:2 or complement thereof, or comprise SEQ ID NO:11 or SEQ ID NO:15. Specific examples of such probe include SEQ ID NO:11 or SEQ ID NO:15. Such probe can further be labeled with at least one fluorophore.

The present invention is still further directed to a DNA detection kit comprising: at least one DNA molecule of sufficient length of contiguous nucleotides homologous or complementary to SEQ ID NO:3, SEQ ID NO:4, SEQ ID NO:5, or SEQ ID NO:6 to function as a DNA primer or probe specific for soybean event MON87701 and/or its progeny. The at least one DNA molecule can comprise SEQ ID NO:1, SEQ ID NO:2, or complement thereof. A specific example of such DNA molecule is SEQ ID NO:1, SEQ ID NO:2, or complement thereof.

The present invention is still further directed to a method of determining zygosity of DNA of a soybean plant genome comprising soybean event MON87701 in a soybean sample. This method comprises: (a) contacting the sample with a first primer pair of SEQ ID NO:12 and SEQ ID NO:13, that when used together in a nucleic acid amplification reaction with soybean event MON87701 DNA, produces an amplicon that is diagnostic for soybean event MON87701; (b) performing a nucleic acid amplification reaction; (c) detecting a first amplicon so produced; (d) contacting the sample with a second primer pair of SEQ ID NO:13 and SEQ ID NO:14, that when used together in a nucleic acid amplification reaction with soybean genomic DNA other than soybean event MON87701 DNA, produces an amplicon that is diagnostic for soybean genomic DNA other than soybean event MON87701 DNA; (e) performing a nucleic acid amplification reaction; and (f) detecting a second amplicon so produced. Detection of both the amplicon that is diagnostic for soybean event MON87701 and the amplicon that is diagnostic for soybean genomic DNA other than soybean event MON87701 DNA indicates that the sample is heterozygous for soybean event MON87701 DNA. Preferably, the first primer pair is further used together with probe of SEQ ID NO:15, and/or the second primer pair is further used with probe of SEQ ID NO:16.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1

Transformation of Soybean A5547 with pMON53570 and Event Selection

The transgenic soybean plant MON87701 was generated by an *Agrobacterium*-mediated transformation of soybean cells with a DNA fragment derived from pMON53570 (FIG. 1). The binary plant transformation vector, pMON53570, contains two plant transformation cassettes or T-DNAs. Each cassette is flanked by right border and left border sequences at the 5' and 3' ends of the transformation cassette, respectively. An expression cassette, presented as SEQ ID NO:7, is used for the expression of an insect toxin. The expression cassette is comprised of a promoter and leader sequence derived from the *Arabidopsis* ribulose 1,5-bisphosphate carboxylase small subunit gene (P-RbcS4, Krebbers et al., (1988) Plant Mol. Biol. 11: 745-759) which is cloned directly upstream of the insect toxin coding sequence, TIC107, which in turn is cloned directly upstream of a terminator sequence derived from the *Glycine max* 7S alpha' beta conglycinin storage protein gene (T-Sphas, see for example, Schuler et al., (1982) Nucleic Acids Res. 10: 8225-8244). The insect toxin coding sequence, TIC107 is presented as SEQ ID NO:8. The nucleic acid sequence set forth as SEQ ID NO:8 is a synthetic or artificial sequence encoding an insecticidal toxin derived from Cry1Ac (U.S. Pat. No. 5,880,275) with a chloroplast transit peptide coding sequence derived from the *Arabidopsis* ribulose 1,5-bisphosphate carboxylase small subunit gene cloned directly upstream of the insect toxin coding sequence.

The plant transformation vector, pMON53570 was mobilized into disarmed *Agrobacterium tumefaciens* strain ABI by electroporation and selected on spectinomycin and chloramphenicol. Explants from Asgrow soybean variety A5547 were transformed with pMON53570 using a method similar to that described in U.S. Pat. No. 5,914,451. Soybean explants and induced *A. tumefaciens* containing pMON53570 were mixed within 14 hours from the time of initiation of seed germination and wounding by sonication. Following wounding, explants were placed in culture for two to five days after which, they were transferred to selection media containing glyphosate for transformed plant cell selection and antibiotics.

Selection and formation of transgenic shoots was allowed to proceed for six to eight weeks. Developing shoots were sampled and assayed by PCR for the presence of the TIC 107 cassette using primers based upon the TIC 107 expression cassette sequence. Approximately 100-R0 transformation events were produced and tested for the presence of a single-copy of the transgene cassette. Southern analysis used as a first pass screen employed a restriction endonuclease that cleaved the expression cassette once. A single EcoRV site was inserted just inside the right border of the expression cassette. This enzyme cleaves with sufficient frequency in the soybean genome as to usually disassociate closely linked copies of the transgene in multiple copy events. TAQMAN® analysis was also performed to confirm copy number in the R0 generation as described below. Forty two of the R0 events demonstrated a single-copy insertion of the transgene cassette and were allowed to self pollinate to generate F1 progeny. Seventy five F1 plants were grown from seed from each of the selected forty two R0 events. A non-lethal spray of glyphosate was applied to all of the F1 progeny. Those F1 progeny in which the glyphosate resistance cassette was unlinked, turned yellow demonstrating the absence of the glyphosate selection cassette. One hundred and fifteen plants were identified as unlinked events. The one hundred and fifteen F1 plants were allowed to recover from the glyphosate application and then tested for insect resistance to feeding against *Anitcarsia gemmatalis* and *Pseudoplusia includens* at R1 and R7 growth stages. All events passed the bioassay criteria of less than 10% feeding against *Anitcarsia* and *Pseudoplusia*.

Southern analysis was performed on the one hundred and fifteen selected F1 plants to confirm the presence of the expression cassette and absence of undesired nucleotide sequences from the transformation vector. Twelve events were selected from the pool of one hundred and fifteen as the most suitable events for further F1 evaluation of copy number by Southern analysis. TAQMAN® and zygosity assays were also performed on the selected F1 events as described below. Out of the twelve F1 selected events, nine demonstrated by preliminary Southern analysis a single copy of the toxin expression cassette. Several lines from the nine events were carried forward to the F2 and F3 generation for further insect trials and genetic characterization. Only a single F1 plant from each line was selected to generate seed for successive generations.

At F3 generation, a more detailed Southern analysis was performed on four selected lines to build a more detailed restriction enzyme map of the inserted expression cassette. Out of the nine events, one event was completely free of backbone, the glyphosate resistance cassette and the plasmid origin of replication. This event was later discovered to have two unlinked insect toxin expression cassettes and gave rise to several lines of progeny. One progeny line also designated event MON87701 was selected at F3 generation based upon its performance characteristics and molecular characterization. Flanking sequence was generated for each of the selected F3 generation lines using inverse PCR as described below. R0 event selection and F1 zygosity analysis were performed as described below using sequences deduced through inverse PCR of the transformed and wild type lines.

Example 2

Isolation of Flanking Sequences Using Inverse PCR

Sequences flanking the T-DNA insertion in MON87701 were determined using inverse PCR as described in Ochman et al., 1990 (PCR Protocols: A guide to Methods and Applications, Academic Press, Inc.). Plant genomic DNA was isolated from both Asgrow A5547 and the transgenic lines from tissue grown under green house conditions for Southern and TAQMAN® analysis. Approximately 1 gram of young trifoliate leaf tissue was combined with liquid nitrogen and ground to a fine powder using a mortar and pestle. DNA was extracted using a Nucleon Plant DNA extraction kit (RPN8511, Amersham, Piscataway, N.J.) according to the manufacturer's protocol. After the final precipitation step, DNAs were resuspended in 0.5 ml of TE (10 mM Tris-HCl pH 8.0, 1 mM EDTA). This method can be modified by one skilled in the art to extract DNA from any tissue of soybean, including, but not limited to seed.

An aliquot of DNA was digested with restriction endonucleases selected based upon restriction analysis of the T-DNA. After self-ligation of restriction fragments, PCR was performed using primers designed from the T-DNA sequence that would amplify sequences extending away from the 5' and 3' ends of the T-DNA. PCR products were separated by agarose gel electrophoresis and purified using a QIAGEN gel purification kit (Qiagen, Valencia, Calif.). The subsequent products were sequenced directly using standard sequencing protocols. The 5' flanking sequence which extends into the right border sequence of the TIC107 expression cassette T-DNA is presented as SEQ ID NO:3 ([C], see FIG. 2). The 3' flanking sequence which extends into the left border sequence of the TIC107 expression cassette T-DNA is presented as SEQ ID NO:4 ([D], see FIG. 2). The portion of the TIC107 expression cassette DNA (SEQ ID NO:7) that was fully integrated into the A5547 genomic DNA is presented as SEQ ID NO:5 ([E], see FIG. 2).

Isolated sequences were compared to the T-DNA sequence to identify the flanking sequence and the co-isolated T-DNA fragment. Confirmation of the presence of the expression cassette was achieved by PCR with primers designed based upon the deduced flanking sequence data and the known T-DNA sequence. The A5547 wild type sequence corresponding to the same region in which the T-DNA was integrated in the transformed line was isolated using primers designed from the flanking sequences in MON87701. The PCR reactions were performed using the Elongase amplification system (Invitrogen, Carlsbad, Calif.). The flanking sequences in MON87701 and the A5547 wild type sequence were analyzed against multiple nucleotide and protein databases. This information was used to examine the relationship of the transgene to the plant genome and to look for the insertion site integrity. The flanking sequence and wild type sequences were used to design primers for TAQMAN® endpoint assays used to identify the events and determine zygosity as described in example 3.

Example 3

Event Specific Endpoint TAQMAN® and Zygosity Assays

The methods used to identify event MON87701 in a sample are described in an event specific endpoint TAQMAN® PCR for which examples of conditions are described in Table 1 and Table 2. The DNA primers used in the endpoint assay are primers SQ1135 (SEQ ID NO:9), SQ1136 (SEQ ID NO:10) and 6FAM™ labeled primer PB63 (SEQ ID NO:11). 6FAM™ is a fluorescent dye product of Applied Biosystems (Foster City, Calif.) attached to the DNA primer. For TAQMAN® MGB probes, the 5' exonuclease activity of Taq DNA polymerase cleaves the probe from the 5'-end, between the fluorophore and quencher. When hybridized to the target DNA strand, quencher and fluorophore are separated enough to produce a fluorescent signal, thus releasing fluorescence.

SQ1135 (SEQ ID NO:9) and SQ1136 (SEQ ID NO:10) when used in these reaction methods with PB63 (SEQ ID NO:11) produce a DNA amplicon that is diagnostic for event MON87701 DNA. The controls for this analysis should include a positive control from soybean containing event MON87701 DNA, a negative control from non-transgenic soybean and a negative control that contains no template DNA.

These assays are optimized for use with an Applied Biosystems GeneAmp PCR System 9700 or Stratagene Robocycler, MJ Engine, Perkin-Elmer 9700, or Eppendorf Mastercycler Gradient thermocycler. Other methods and apparatus known to those skilled in the art that produce amplicons that identify the event MON87701 DNA is within the skill of the art.

Proceed with the DNA amplification in a Stratagene Robocycler, or MJ Engine, or Perkin-Elmer 9700, or Eppendorf Mastercycler Gradient thermocycler or Applied Biosystems GeneAmp PCR System 9700 or MJ Research DNA Engine PTC-225 thermal cycler using the following cycling parameters. When running the PCR in the Eppendorf Mastercycler Gradient or MJ Engine, the thermocycler should be run in the calculated mode. When running the PCR in the Perkin-Elmer 9700, run the thermocycler with the ramp speed set at maximum.

TABLE 1

Soybean MON87701 Event Specific Endpoint TAQMAN ® PCR

| Step | Reagent | Volume | Comments |
|---|---|---|---|
| 1 | 18 megohm water | adjust for final volume of 10 µl | |
| 2 | 2X Universal Master Mix (Contains dNTPs, enzyme and buffer) | 5.0 µl | 1X final concentration of dNTPs, enzyme and buffer |
| 3 | Primer-1 and Primer-2 Mix (resuspended in 18 megohm water to a concentration of 20 uM for each primer) Example: In a microcentrifuge tube, the following should be added to achieve 500 ul at a final concentration of 20 uM: 100 ul of Primer SQ1135 (SEQ ID NO: 9) at a concentration of 100 uM 100 ul of Primer SQ1136 (SEQ ID NO: 10) at a concentration of 100 uM 300 ul of 18 megohm water | 0.5 µl | 1.0 µM final concentration |
| 4 | Event 6-FAM ™ MGB Probe PB63 (SEQ ID NO: 11) (resuspended in 18 megohm water to a concentration of 10 uM) | 0.2 µl | 0.2 µM final concentration |
| 5 | Extracted DNA (template): 1. Leaf Samples to be analyzed 2. Negative control (non-transgenic DNA) 3. Negative water control (no template control) 4. Positive control GM_A19459A DNA | 3.0 µl | |

TABLE 2

Endpoint TAQMAN ® thermocycler conditions

| Cycle No. | Settings |
|---|---|
| 1 | 50° C. 2 minutes |
| 1 | 95° C. 10 minutes |
| 10 | 95° C. 15 seconds |
|  | 64° C. 1 minute |
|  | −1° C./cycle |
| 30 | 95° C. 15 seconds |
|  | 54° C. 1 minute |
| 1 | 10° C. Forever |

R0 plants demonstrating the presence of the TIC107 expression cassette were allowed to develop into fully mature plants. The R0 plants were evaluated for the occurrence of linkage between the TIC107 expression cassette and the glyphosate resistance expression cassette using Southern analysis with a DNA restriction enzyme known to not cut into both cassettes and the region between each cassette in the plasmid, PacI. Probes designed based upon the sequences of the glyphosate resistance cassette, the TIC107 cassette and the origin of replication (OR-Ec.oriV-RK2) which resides in between the two expression cassettes in pMON53570 were used to probe Southern blots to determine linkage. The R0 plants were also evaluated for copy number of the TIC107 expression cassette using a combination of Southern analysis and endpoint TAQMAN®. R0 plants demonstrating an unlinked relationship between the Glyphosate resistance cassette and the TIC107 expression cassette were allowed to self pollinate and produce F1 progeny.

F1 plants were assayed for the absence of the glyphosate resistance cassette due to segregation occurring in the F1 population from unlinked self-pollinated R0 transformed events. A non-lethal application of glyphosate was applied to the F1 individuals. Those plants in which the resistance cassette was lost due to segregation demonstrated damage from the application of glyphosate. These plants were allowed to recover and develop normally. Zygosity assays for the TIC107 expression cassette were performed upon F1 plants using a TAQMAN® endpoint assay as described below.

The methods used to determine zygosity for event MON87701 in a sample are described in an event specific zygosity endpoint TAQMAN PCR for which examples of conditions are described in Table 3 and Table 4. The DNA primers used in the zygosity assay are primers SQ3443 (SEQ ID NO:12), SQ3445 (SEQ ID NO:13), SQ3446 (SEQ ID NO:14), 6FAM™-labeled primer PB1111 (SEQ ID NO:15) and VIC™-labeled primer PB 1112 (SEQ ID NO:16). 6FAM™ and VIC™ are fluorescent dye products of Applied Biosystems (Foster City, Calif.) attached to the DNA primers. For TAQMAN MGB probes, the 5' exonuclease activity of Taq DNA polymerase cleaves the probe from the 5'-end, between the fluorophore and quencher. When hybridized to the target DNA strand, quencher and fluorophore are separated enough to produce a fluorescent signal, thus releasing fluorescence.

SQ3443 (SEQ ID NO:12) and SQ3445 (SEQ ID NO:13) when used in these reaction methods with PB1111 (SEQ ID NO:15) produce a DNA amplicon that is diagnostic for event MON87701 DNA. The controls for this analysis should include a positive control from soybean containing event MON87701 DNA, a negative control from non-transgenic soybean and a negative control that contains no template DNA.

SQ3445 (SEQ ID NO:13) and SQ3446 (SEQ ID NO:14) when used in these reaction methods with PB1112 (SEQ ID NO:16) produce a DNA amplicon that is diagnostic for the wild type allele.

Heterozygosity is determined by the presence of both amplicons demonstrated by the liberation of fluorescent signal from both probes PB1111 and PB1112.

These assays are optimized for use with an Applied Biosystems GeneAmp PCR System 9700 or Stratagene Robocycler, MJ Engine, Perkin-Elmer 9700, or Eppendorf Mastercycler Gradient thermocycler. Other methods and apparatus known to those skilled in the art that produce amplicons that identify the event MON87701 DNA is within the skill of the art.

Proceed with the DNA amplification in a Stratagene Robocycler, MJ Engine, Perkin-Elmer 9700, or Eppendorf Mastercycler Gradient thermocycler or Applied Biosystems GeneAmp PCR System 9700 or MJ Research DNA Engine PTC-225 thermal cycler using the following cycling parameters. When running the PCR in the Eppendorf Mastercycler Gradient or MJ Engine, the thermocycler should be run in the calculated mode. When running the PCR in the Perkin-Elmer 9700, run the thermocycler with the ramp speed set at maximum.

TABLE 3

Soybean MON87701 Event Specific Zygosity Endpoint TAQMAN ® PCR

| Step | Reagent | Volume | Comments |
|---|---|---|---|
| 1 | 18 megohm water | adjust for final volume of 10 μl | |
| 2 | 2X Universal Master Mix (Contains dNTPs, enzyme and buffer) | 5.0 μl | 1X final concentration of dNTPs, enzyme and buffer |
| 3 | Zygosity Primer-1, Primer-2, & Primer-3 Mix (resuspended in 18 megohm water to a concentration of 20 uM for each primer) Example: In a microcentrifuge tube, the following should be added to achieve 500 ul at a final concentration of 20 uM: 100 ul of Primer SQ3443 (SEQ ID NO: 12) at a concentration of 100 uM 100 ul of Primer SQ3445 (SEQ ID NO: 13) at a concentration of 100 uM 100 ul of Primer SQ3446 (SEQ ID NO: 14) at a concentration of 100 uM 200 ul of 18 megohm water | 0.5 μl | 1.0 μM final concentration |
| 4 | Event 6-FAM ™ MGB Probe PB1111 (SEQ ID NO: 15) (resuspended in 18 megohm water to a concentration of 10 uM) | 0.2 μl | 0.2 μM final concentration |
| 5 | WT VIC ™ MGB Probe PB1112 (SEQ ID NO: 16) (resuspended in 18 megohm water to a concentration of 10 uM) | 0.2 μl | 0.2 μM final concentration |

TABLE 3-continued

Soybean MON87701 Event Specific Zygosity Endpoint TAQMAN ® PCR

| Step | Reagent | Volume | Comments |
|---|---|---|---|
| 6 | Extracted DNA (template): 1. Leaf Samples to be analyzed 2. Negative control (non-transgenic DNA) 3. Negative water control (no template control) 4. Positive control Homozygous GM_A19459A DNA 5. Positive control Hemizygous GM_A19459A DNA | 3.0 µl | |

TABLE 4

Zygosity Endpoint TAQMAN ® thermocycler conditions

| Cycle No. | Settings |
|---|---|
| 1 | 50° C. 2 minutes |
| 1 | 95° C. 10 minutes |
| 10 | 95° C. 15 seconds |
| | 64° C. 1 minute |
| | −1° C./cycle |
| 30 | 95° C. 15 seconds |
| | 54° C. 1 minute |
| 1 | 10° C. Forever |

The event MON87701 F1 plants were also tested for resistance to *Anticarsia* and *Pseudoplusia*. Resistance was defined as less than 10% feeding in the R1 and R7 growth stages. Copy number analysis was further performed on selected F1 individuals using Southern analysis and a restriction endonuclease known to cut in one single location within the TIC107 expression cassette, EcoRV. Expression of the TIC107 protein in the F1 population was confirmed using protein test strips (EnviroLogix, QuickStix™ Kit for Cry1Ac Cotton Leaf & Seed, Cat. # AS 003, Portland, Me. 04103) following the manufacturer's protocol. Southern analysis was performed on selected events in the F3 population to confirm the presence of a single intact T-DNA insert. Ultimate line selection was based upon performance characteristics in field testing, protein expression and molecular characterization.

Example 4

Identification of Event MON87701 in any MON87701 Breeding Event

The following example describes how one may identify the MON87701 event within progeny of any breeding event using MON87701 soybean.

DNA event primer pairs are used to produce an amplicon diagnostic for soybean event MON87701. An amplicon diagnostic for MON87701 comprises at least one junction sequence, SEQ ID NO:1 or SEQ ID NO:2 ([A] and [B], respectively as illustrated in FIG. 2). SEQ ID NO:1 ([A] of FIG. 2) is a nucleotide sequence corresponding to the junction of the 5' flanking sequence (positions 5748 through 5757 of SEQ ID NO:3 [C], see FIG. 2) and the integrated right border of the TIC107 expression cassette (positions 1 through 10 of SEQ ID NO:5 [E], see FIG. 2). SEQ ID NO:1 also corresponds to positions 5748 to 5767 of the 5' flanking sequence, SEQ ID NO:3 ([C], see FIG. 2). SEQ ID NO:2 ([B], see FIG. 2) is a nucleotide sequence corresponding to the junction of the integrated left border of the TIC107 expression cassette (positions 6417 through 6426 of SEQ ID NO:5 [E], see FIG. 2) and the 3' flanking sequence (positions 379 through 388 of SEQ ID NO:4 [D], see FIG. 2). SEQ ID NO:2 ([C], see FIG. 2) also corresponds to positions 369 to 388 of the 3' flanking sequence, SEQ ID NO:4 ([D], see FIG. 2).

Event primer pairs that will produce a diagnostic amplicon for MON87701 include primer pairs based upon the flanking sequences and the inserted TIC107 expression cassette. To acquire a diagnostic amplicon in which at least 11 nucleotides of SEQ ID NO:1 is found, one would design a forward primer based upon SEQ ID NO:3 from bases 1 through 5747 and a reverse primer based upon the TIC107 inserted expression cassette, SEQ ID NO:5 from positions 10 through 6416. To acquire a diagnostic amplicon in which at least 11 nucleotides of SEQ ID NO:2 is found, one would design a forward primer based upon the TIC 107 inserted expression cassette, SEQ ID NO:5 from positions 10 through 6416 and a reverse primer based upon the 3' flanking sequence, SEQ ID NO:4 from bases 389 through 2611. For practical purposes, one should design primers which produce amplicons of a limited size range, preferably between 200 to 1000 bases. Smaller sized amplicons in general are more reliably produced in PCR reactions, allow for shorter cycle times, and can be easily separated and visualized on agarose gels or adapted for use in endpoint TAQMAN®-like assays. In addition, amplicons produced using said primer pairs can be cloned into vectors, propagated, isolated and sequenced or can be sequenced directly with methods well established in the art. Any primer pair derived from the combination of SEQ ID NO:3 and SEQ ID NO:5 or the combination of SEQ ID NO:4 and SEQ ID NO:5 that are useful in a DNA amplification method to produce an amplicon diagnostic for MON87701 or progeny thereof is an aspect of the present invention. Any single isolated DNA polynucleotide primer molecule comprising at least 11 contiguous nucleotides of SEQ ID NO:3, or its complement that is useful in a DNA amplification method to produce an amplicon diagnostic for MON87701 or progeny thereof is an aspect of the present invention. Any single isolated DNA polynucleotide primer molecule comprising at least 11 contiguous nucleotides of SEQ ID NO:4, or its complement that is useful in a DNA amplification method to produce an amplicon diagnostic for MON87701 or progeny thereof is an aspect of the present invention. Any single isolated DNA polynucleotide primer molecule comprising at least 11 contiguous nucleotides of SEQ ID NO:5, or its complement that is useful in a DNA amplification method to produce an amplicon diagnostic for MON87701 or progeny thereof is an aspect of the present invention.

An example of the amplification conditions for this analysis is illustrated in Table 5 and Table 6. However, any modification of these methods or the use of DNA primers homologous or complementary to SEQ ID NO:3 or SEQ ID NO:4 or DNA sequences of the genetic elements contained in the transgene insert (SEQ ID NO:5) of MON87701 that produce an amplicon diagnostic for MON87701, is within the art. A diagnostic amplicon comprises a DNA molecule homologous or complementary to at least one transgene/genomic junction DNA (SEQ ID NO:1 or SEQ ID NO:2), or a substantial portion thereof.

An analysis for event MON87701 plant tissue sample should include a positive tissue control from event MON87701, a negative control from a soybean plant that is not event MON87701, for example, but not limited to A5547, and a negative control that contains no soybean genomic DNA. A primer pair that will amplify an endogenous soybean DNA molecule will serve as an internal control for the DNA amplification conditions. Additional primer sequences can be selected from SEQ ID NO:3, SEQ ID NO:4, or SEQ ID NO:5 by those skilled in the art of DNA amplification methods, and conditions selected for the production of an amplicon by the methods shown in Table 5 and Table 6 may differ, but result in an amplicon diagnostic for event MON87701 DNA. The use of these DNA primer sequences with modifications to the methods of Table 5 and Table 6 are within the scope of the invention. The amplicon produced by at least one DNA primer sequence derived from SEQ ID NO:3, SEQ ID NO:4, or SEQ ID NO:5 that is diagnostic for MON87701 is an aspect of the invention.

DNA detection kits that contain at least one DNA primer derived from SEQ ID NO:3, SEQ ID NO:4, or SEQ ID NO:5, that when used in a DNA amplification method, produces a diagnostic amplicon for MON87701 or its progeny is an aspect of the invention. A soybean plant or seed, wherein its genome will produce an amplicon diagnostic for MON87701 when tested in a DNA amplification method is an aspect of the invention. The assay for the MON87701 amplicon can be performed by using an Applied Biosystems GeneAmp PCR System 9700 or Stratagene Robocycler, or MJ Engine, or Perkin-Elmer 9700, or Eppendorf Mastercycler Gradient thermocycler or any other amplification system that can be used to produce an amplicon diagnostic of MON87701 as shown in Table 6.

TABLE 5

Soybean MON87701 Event Specific PCR Assay

| Step | Reagent | Volume | Comments |
|---|---|---|---|
| 1 | 18 megohm water | adjust for final volume of 10 μl | |
| 2 | 2X Universal Master Mix (Contains dNTPs, enzyme and buffer) | 5.0 μl | 1X final concentration of dNTPs, enzyme and buffer |
| 3 | Primer-1 and Primer-2 Mix (resuspended in 18 megohm water to a concentration of 20 uM for each primer) Example: In a microcentrifuge tube, the following should be added to achieve 500 ul at a final concentration of 20 uM: 100 ul of Primer 1 at a concentration of 100 uM 100 ul of Primer 2 at a concentration of 100 uM 300 ul of 18 megohm water | 0.5 μl | 1.0 μM final concentration |
| 5 | Extracted DNA (template) 50 ng of genomic DNA: Leaf Samples to be analyzed Negative control (non-transgenic DNA) Negative water control (no template control) Positive control MON88701 DNA | 3.0 μl | |

TABLE 6

Soybean MON87701 Event Thermocycler Conditions

| Cycle No. | Settings |
|---|---|
| 1 | 50° C. 2 minutes |
| 1 | 95° C. 10 minutes |
| 10 | 95° C. 15 seconds |
| | 64° C. 1 minute |
| | −1° C./cycle |
| 30 | 95° C. 15 seconds |
| | 54° C. 1 minute |
| 1 | 10° C. Forever |

A deposit of the soybean event MON87701 seed disclosed above and recited in the claims, has been made under the Budapest Treaty with the American Type Culture Collection (ATCC), 10801 University Boulevard, Manassas, Va. 20110. The ATCC deposit was made on Jan. 31, 2007. The ATCC accession number is PTA-8194. The deposit will be maintained in the depository for a period of 30 years, or 5 years after the last request, or for the effective life of the patent, whichever is longer, and will be replaced as necessary during that period.

Having illustrated and described the principles of the present invention, it should be apparent to persons skilled in the art that the invention can be modified in arrangement and detail without departing from such principles. We claim all modifications that are within the spirit and scope of the appended claims.

We claim:

1. A DNA molecule comprising the nucleotide sequence of SEQ ID NO:3, SEQ ID NO:4, SEQ ID NO:6 or complement thereof.

2. The DNA molecule of claim 1, consisting essentially of the nucleotide sequence of SEQ ID NO:3 from positions 1 to 5757, the nucleotide sequence of SEQ ID NO:5 from positions 1 to 6426, and the nucleotide sequence of SEQ ID NO:4 from positions 379 to 2611, or complement thereof.

3. The DNA molecule of claim 1, consisting essentially of the nucleotide sequence of SEQ ID NO:6 or complement thereof.

4. A soybean plant, or parts thereof, comprising the DNA molecule of claim 2 or 3.

5. Seed of the soybean plant of claim 4, wherein said seed comprises said DNA molecule.

6. A composition derived from the soybean plant, or parts thereof, as set forth in claim 4, wherein said composition comprises a detectable amount of said DNA molecule, and wherein said composition is a commodity product selected from the group consisting of soybean meal, soy flour, soy protein concentrate, soy protein isolates, texturized soy protein concentrate, hydrolyzed soy protein, soybean oil and whipped topping.

7. A method of producing an insect resistant soybean plant comprising:
(a) crossing the soybean plant of claim 4 with another soybean plant;
(b) obtaining at least one progeny plant derived from the cross of (a); and
(c) selecting progeny that comprises nucleotide sequences of SEQ ID NO:1 and SEQ ID NO:2, wherein said selected progeny is an insect resistant soybean plant.

8. The method of claim 7, wherein said selecting step (c) includes subjecting said at least one progeny plant obtained from (b) to a nucleic acid amplification reaction, wherein progeny that produces an amplicon comprising at least one nucleotide sequence of SEQ ID NO:3, SEQ ID NO:4, SEQ ID NO:5 or SEQ ID NO:6 is selected, or subjecting said at least one progeny plant obtained from (b) to a nucleic acid hybridization reaction, wherein progeny hybridizing to a probe that hybridizes under stringent conditions with one or more DNA sequence selected from SEQ ID NO:1 and SEQ ID NO:2 is selected.

9. A method for protecting a soybean plant from insect infestation, comprising providing in the diet of a Lepidopteran pest of soybean an insecticidally effective amount of cell(s) or tissue(s) of the soybean plant, or parts thereof, of claim 4.

10. The method of claim 9, wherein said Lepidopteran pest is selected from the group consisting of *Anticarsia, Pseudoplusia, Epinotia, Spilosoma, Helicoverpa, Spodoptera* and *Rachiplusia*.

11. A transgenic soybean plant cell comprising DNA encoding TIC107 and DNA having nucleotide sequences of SEQ ID NO:1 and SEQ ID NO:2.

12. An insect resistant soybean plant, or parts thereof, comprising the transgenic soybean plant cell of claim 11.

13. Seed of the insect resistant soybean plant of claim 12, wherein said seed comprises said DNA encoding TIC107 and said DNA having nucleotide sequences of SEQ ID NO:1 and SEQ ID NO:2.

14. Seed of soybean plant designated MON87701, having representative sample deposited with the American Type Culture Collection (ATCC) under accession number PTA-8194.

15. A soybean plant MON87701 or parts thereof produced by growing the seed of claim 14.

16. A soybean plant, seed, or parts thereof, comprising soybean event MON87701.

17. A soybean plant, seed, or parts thereof, capable of producing a MON87701 diagnostic amplicon.

18. The soybean plant, seed, or parts thereof, of claim 17, wherein said MON87701 diagnostic amplicon comprises a DNA molecule homologous or complementary to at least one transgene/genomic junction DNA (SEQ ID NO:1 or SEQ ID NO:2), or a substantial portion thereof.

19. A composition derived from the transgenic soybean plant, or parts thereof, as set forth in any one of claims 12 and 15 to 18, wherein said composition comprises a detectable amount of said DNA encoding TIC107 and said DNA having nucleotide sequences of SEQ ID NO:1 and SEQ ID NO:2, and wherein said composition is a commodity product selected from the group consisting of soybean meal, soy flour, soy protein concentrate, soy protein isolates, texturized soy protein concentrate, hydrolyzed soy protein, soybean oil and whipped topping.

20. A method of producing an insect resistant soybean plant comprising:
(a) sexually crossing a first insect resistant soybean plant MON87701 having representative seed deposited with the American Type Culture Collection (ATCC) under accession number PTA-8194 and a second parent soybean plant that lacks insect resistance, thereby producing a plurality of progeny plants; and
(b) selecting a progeny plant that is insect resistant.

21. The method of claim 20, further comprising backcrossing the progeny plant that is insect resistant to the second parent soybean plant, thereby producing a plant that is insect resistant.

22. A method of producing an insect resistant soybean plant, comprising:
(a) crossing the soybean plant of any one of claims 12 and 15 to 18 with another soybean plant; and
(b) selecting a progeny plant that is insect resistant by analyzing for the presence of at least one nucleotide sequence of SEQ ID NO:1 and SEQ ID NO:2.

23. The method of claim 22, wherein said selecting step (b) includes subjecting the progeny plant to a nucleic acid amplification reaction, wherein progeny plant that produces an amplicon comprising at least one nucleotide sequence of SEQ ID NO:1 and SEQ ID NO:2 is selected, or subjecting the progeny plant to a nucleic acid hybridization reaction, wherein progeny hybridizing to a probe that hybridizes under stringent conditions with one or more DNA sequence selected from SEQ ID NO:1 and SEQ ID NO:2 is selected.

24. A method of producing an insect resistant soybean plant, comprising
(a) transforming a soybean plant cell with DNA encoding TIC107 and DNA having nucleotide sequences of SEQ ID NO:1 and SEQ ID NO:2; and
(b) regenerating a soybean plant from said transformed cell, wherein said soybean plant comprises said DNA encoding TIC107 and said DNA having nucleotide sequences of SEQ ID NO:1 and SEQ ID NO:2 and is insect resistant.

* * * * *